(12) United States Patent
Grady, Jr. et al.

(10) Patent No.: US 9,308,034 B2
(45) Date of Patent: Apr. 12, 2016

(54) BONE PLATE

(71) Applicant: DePuy Synthes Products, Inc., Raynham, MA (US)

(72) Inventors: Mark P. Grady, Jr., West Chester, PA (US); René Haag, West Chester, PA (US); Scott Didomenico, Raynham, MA (US); Kenny Koay, West Chester, PA (US); Jeffrey W. Mast, Reno, NV (US); Brett R. Bolhofner, St. Petersburg, FL (US); Keith A. Mayo, Gig Harbor, WA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/930,411

(22) Filed: Jun. 28, 2013

(65) Prior Publication Data

US 2013/0296943 A1 Nov. 7, 2013

Related U.S. Application Data

(63) Continuation of application No. 13/092,625, filed on Apr. 22, 2011, which is a continuation of application No. 10/843,113, filed on May 11, 2004, now Pat. No. 7,951,176.

(60) Provisional application No. 60/474,279, filed on May 30, 2003.

(51) Int. Cl.
*A61B 17/80* (2006.01)
*A61B 17/74* (2006.01)
*A61B 17/86* (2006.01)

(52) U.S. Cl.
CPC .............. *A61B 17/809* (2013.01); *A61B 17/74* (2013.01); *A61B 17/746* (2013.01);
(Continued)

(58) Field of Classification Search
USPC ........... 606/64, 65, 69, 70, 98, 280, 281, 286, 606/287, 288, 289, 291, 297, 902
See application file for complete search history.

(56) References Cited

U.S. PATENT DOCUMENTS 327,296 A * 9/1885 McGinnis ..................... 411/454
2,414,882 A 1/1947 Longfellow
(Continued)

FOREIGN PATENT DOCUMENTS

CH 611147 5/1979
CH 670755 7/1989
(Continued)

OTHER PUBLICATIONS

ACE Symmetry™, "Curves in All the Right Places", Titanium Upper Extremity Plates, Ace Medical Company, 1996, 3 pages.

*Primary Examiner* — Christian Sevilla
(74) *Attorney, Agent, or Firm* — Baker & Hostetler LLP

(57) ABSTRACT

A bone plate includes (a) a body having a first surface which, in an operative configuration, faces away from a bone on which the plate is to be mounted and a second surface, which in the operative configuration, faces the bone, the body including a first section extending along a first longitudinal axis and a second section extending along a second longitudinal axis angled with respect to the first longitudinal axis; (b) a first hole extending through the body from the first surface to the second surface and defining a first hole axis, the first hole being structured to lockingly engage a head of a first bone anchor inserted therein such that a shaft of the first bone anchor extends along the first hole axis; and (c) a second hole extending through the body and spaced apart from the first hole. The second hole defines a second hole axis and is structured to lockingly engage a head of a second bone anchor inserted therein such that a shaft of the second bone anchor extends along the second hole axis. The first and second hole axes defines a single plane and intersecting at a point on a side of the bone plate facing the second surface.

27 Claims, 18 Drawing Sheets

(52) U.S. Cl.
CPC ........ *A61B 17/8052* (2013.01); *A61B 17/8014* (2013.01); *A61B 17/8057* (2013.01); *A61B 17/8066* (2013.01); *A61B 17/86* (2013.01)

(56) References Cited

U.S. PATENT DOCUMENTS

| | | | |
|---|---|---|---|
| 2,443,363 A | 6/1948 | Townsend et al. | |
| 2,496,126 A | 1/1950 | Harboush | |
| 2,526,959 A | 10/1950 | Lorenzo | |
| 2,612,159 A | 9/1952 | Collison | |
| 2,627,855 A | 2/1953 | Price | |
| 2,699,774 A | 1/1955 | Livingston | |
| 2,772,676 A | 12/1956 | Pohl | |
| 2,801,631 A | 8/1957 | Charnley | |
| 2,874,691 A | 2/1959 | Mason | |
| 3,025,853 A | 3/1962 | Mason | |
| 3,374,786 A | 3/1968 | Callender, Jr. | |
| 3,489,143 A | 1/1970 | Halloran | |
| 3,552,389 A | 1/1971 | Allgower et al. | |
| 3,561,437 A | 2/1971 | Orlich | |
| 3,577,601 A | 5/1971 | Mariani | |
| 3,668,972 A | 6/1972 | Allgower et al. | |
| 3,695,259 A | 10/1972 | Yost | |
| 3,716,050 A | 2/1973 | Johnston | |
| 3,779,240 A | 12/1973 | Kondo | |
| 3,782,374 A | 1/1974 | Fischer | |
| 3,824,995 A | 7/1974 | Getscher et al. | |
| 3,842,825 A | 10/1974 | Wagner | |
| RE28,841 E | 6/1976 | Allgower et al. | |
| 3,996,931 A | 12/1976 | Callender, Jr. | |
| 4,009,712 A | 3/1977 | Burstein et al. | |
| 4,040,129 A | 8/1977 | Steinemann et al. | |
| 4,095,591 A | 6/1978 | Graham, Jr. et al. | |
| 4,120,298 A | 10/1978 | Fixel | |
| 4,172,452 A | 10/1979 | Forte et al. | |
| 4,219,015 A | 8/1980 | Steinemann | |
| 4,236,512 A | 12/1980 | Aginsky | |
| 4,269,180 A | 5/1981 | Dall et al. | |
| 4,379,451 A | 4/1983 | Getscher | |
| 4,408,601 A | 10/1983 | Wenk | |
| 4,438,762 A | 3/1984 | Kyle | |
| 4,454,876 A | 6/1984 | Mears | |
| RE31,628 E | 7/1984 | Allgower et al. | |
| 4,484,570 A | 11/1984 | Sutter et al. | |
| 4,488,543 A | 12/1984 | Tornier | |
| 4,493,317 A | 1/1985 | Klaue | |
| 4,494,535 A | 1/1985 | Haig | |
| 4,513,744 A | 4/1985 | Klaue | |
| 4,565,193 A | 1/1986 | Streli | |
| 4,612,920 A | 9/1986 | Lower | |
| 4,616,638 A | 10/1986 | Griggs | |
| 4,617,922 A | 10/1986 | Griggs | |
| 4,621,629 A | 11/1986 | Koeneman | |
| 4,628,923 A | 12/1986 | Medoff | |
| 4,651,724 A | 3/1987 | Berentey et al. | |
| 4,657,001 A | 4/1987 | Fixel | |
| 4,776,329 A | 10/1988 | Treharne | |
| 4,776,330 A | 10/1988 | Chapman et al. | |
| 4,791,918 A * | 12/1988 | Von Hasselbach | 606/65 |
| 4,795,473 A | 1/1989 | Grimes | |
| 4,800,874 A | 1/1989 | David et al. | |
| 4,838,252 A | 6/1989 | Klaue | |
| 4,848,328 A | 7/1989 | Laboureau et al. | |
| 4,867,144 A | 9/1989 | Karas et al. | |
| 4,903,691 A | 2/1990 | Heinl | |
| 4,905,680 A | 3/1990 | Tunc | |
| 4,927,421 A | 5/1990 | Goble et al. | |
| 4,955,886 A | 9/1990 | Pawluk | |
| 4,957,496 A | 9/1990 | Schmidt | |
| 4,957,497 A | 9/1990 | Hoogland et al. | |
| 4,964,403 A | 10/1990 | Karas et al. | |
| 4,966,599 A | 10/1990 | Pollock | |
| 4,973,332 A | 11/1990 | Kummer | |
| 4,973,333 A | 11/1990 | Treharne | |
| 4,988,350 A | 1/1991 | Herzberg | |
| 5,002,544 A | 3/1991 | Klaue et al. | |
| 5,006,120 A | 4/1991 | Carter | |
| 5,015,248 A | 5/1991 | Burstein et al. | |
| 5,041,114 A | 8/1991 | Chapman et al. | |
| 5,041,116 A | 8/1991 | Wilson | |
| 5,085,660 A | 2/1992 | Lin | |
| 5,087,260 A | 2/1992 | Fixel | |
| 5,108,399 A | 4/1992 | Eitenmuller et al. | |
| 5,108,449 A | 4/1992 | Gray | |
| 5,116,336 A | 5/1992 | Frigg | |
| 5,127,914 A * | 7/1992 | Calderale et al. | 606/65 |
| 5,129,901 A | 7/1992 | Decoste | |
| 5,147,363 A | 9/1992 | Harle | |
| 5,151,103 A | 9/1992 | Tepic et al. | |
| 5,152,794 A | 10/1992 | Davidson | |
| 5,190,544 A | 3/1993 | Chapman et al. | |
| 5,197,966 A | 3/1993 | Sommerkamp | |
| 5,269,784 A | 12/1993 | Mast | |
| 5,275,601 A | 1/1994 | Gogolewski et al. | |
| 5,290,281 A | 3/1994 | Tschakaloff | |
| 5,300,074 A * | 4/1994 | Frigg | 606/67 |
| 5,304,180 A | 4/1994 | Slocum | |
| 5,324,290 A | 6/1994 | Zdeblick et al. | |
| 5,324,292 A | 6/1994 | Meyers | |
| 5,356,410 A | 10/1994 | Pennig | |
| 5,360,429 A | 11/1994 | Jeanson et al. | |
| 5,364,398 A | 11/1994 | Chapman et al. | |
| 5,364,399 A | 11/1994 | Lowery et al. | |
| 5,372,598 A | 12/1994 | Luhr et al. | |
| 5,376,126 A | 12/1994 | Lin | |
| 5,395,372 A | 3/1995 | Holt et al. | |
| 5,413,577 A | 5/1995 | Pollock | |
| 5,429,641 A | 7/1995 | Gotfried | |
| 5,458,654 A | 10/1995 | Tepic | |
| 5,462,547 A | 10/1995 | Weigum | |
| 5,484,439 A | 1/1996 | Olson et al. | |
| 5,514,138 A | 5/1996 | McCarthy | |
| 5,522,902 A | 6/1996 | Yuan et al. | |
| 5,531,746 A | 7/1996 | Errico et al. | |
| 5,586,985 A | 12/1996 | Putnam et al. | |
| 5,591,168 A | 1/1997 | Judet et al. | |
| 5,601,553 A * | 2/1997 | Trebing et al. | 606/86 B |
| 5,607,427 A | 3/1997 | Tschakaloff | |
| 5,647,872 A | 7/1997 | Gilbert et al. | |
| 5,658,339 A | 8/1997 | Tronzo et al. | |
| 5,662,655 A | 9/1997 | Laboureau et al. | |
| 5,674,222 A | 10/1997 | Berger et al. | |
| 5,676,667 A | 10/1997 | Hausman | |
| 5,681,311 A | 10/1997 | Foley et al. | |
| D385,963 S | 11/1997 | Hansson | |
| 5,693,055 A | 12/1997 | Zahiri et al. | |
| 5,702,396 A | 12/1997 | Hoenig et al. | |
| 5,702,399 A | 12/1997 | Kilpela et al. | |
| 5,709,682 A | 1/1998 | Medoff | |
| 5,709,686 A | 1/1998 | Talos et al. | |
| 5,718,704 A | 2/1998 | Medoff | |
| 5,718,705 A | 2/1998 | Sammarco | |
| 5,728,099 A | 3/1998 | Tellman et al. | |
| 5,733,287 A | 3/1998 | Tepic et al. | |
| 5,741,256 A * | 4/1998 | Bresina | 606/62 |
| 5,743,912 A | 4/1998 | Lahille et al. | |
| 5,749,872 A | 5/1998 | Kyle et al. | |
| 5,772,662 A | 6/1998 | Chapman et al. | |
| 5,779,706 A | 7/1998 | Tschakaloff | |
| 5,797,916 A | 8/1998 | McDowell | |
| 5,800,553 A | 9/1998 | Albrektsson et al. | |
| 5,810,821 A | 9/1998 | Vandewalle | |
| 5,810,822 A | 9/1998 | Mortier | |
| 5,810,823 A | 9/1998 | Klaue et al. | |
| 5,853,413 A | 12/1998 | Carter et al. | |
| 5,921,988 A | 7/1999 | Legrand | |
| 5,931,839 A | 8/1999 | Medoff | |
| 5,938,664 A | 8/1999 | Winquist et al. | |
| 5,954,722 A | 9/1999 | Bono | |
| 5,968,046 A | 10/1999 | Castleman | |
| 5,968,047 A | 10/1999 | Reed | |
| 5,973,223 A | 10/1999 | Tellman et al. | |
| 5,976,139 A | 11/1999 | Bramlet | |
| 6,007,535 A | 12/1999 | Rayhack et al. | |

(56) References Cited

U.S. PATENT DOCUMENTS

| | | | |
|---|---|---|---|
| 6,022,352 A | 2/2000 | Vandewalle | |
| 6,066,141 A | 5/2000 | Dall et al. | |
| 6,096,040 A | 8/2000 | Esser | |
| 6,113,603 A | 9/2000 | Medoff | |
| 6,129,728 A | 10/2000 | Schumacher et al. | |
| 6,152,927 A | 11/2000 | Farris et al. | |
| 6,183,474 B1 | 2/2001 | Bramlet et al. | |
| 6,183,475 B1 | 2/2001 | Lester et al. | |
| 6,187,007 B1 | 2/2001 | Frigg et al. | |
| 6,206,881 B1 | 3/2001 | Frigg et al. | |
| 6,221,073 B1 | 4/2001 | Weiss et al. | |
| 6,221,075 B1 | 4/2001 | Tormala et al. | |
| D443,060 S | 5/2001 | Benirschke et al. | |
| 6,224,602 B1 | 5/2001 | Hayes | |
| 6,235,032 B1 | 5/2001 | Link | |
| 6,283,969 B1 | 9/2001 | Grusin et al. | |
| 6,287,309 B1 | 9/2001 | Baccelli et al. | |
| 6,290,703 B1 | 9/2001 | Ganem | |
| 6,322,562 B1 | 11/2001 | Wolter | |
| 6,325,803 B1 | 12/2001 | Schumacher et al. | |
| 6,338,734 B1 | 1/2002 | Burke et al. | |
| 6,342,055 B1 | 1/2002 | Eisermann et al. | |
| 6,348,052 B1 | 2/2002 | Sammarco | |
| 6,350,265 B1 | 2/2002 | Blaustein et al. | |
| 6,355,041 B1 | 3/2002 | Martin | |
| 6,355,042 B2 | 3/2002 | Winquist et al. | |
| 6,358,250 B1 | 3/2002 | Orbay | |
| 6,364,882 B1 | 4/2002 | Orbay | |
| 6,379,359 B1 | 4/2002 | Dahners | |
| D458,374 S | 6/2002 | Bryant et al. | |
| D458,683 S | 6/2002 | Bryant et al. | |
| D458,684 S | 6/2002 | Bryant et al. | |
| D458,996 S | 6/2002 | Bryant et al. | |
| 6,440,131 B1 | 8/2002 | Haidukewych | |
| 6,440,135 B2 | 8/2002 | Orbay et al. | |
| D463,557 S | 9/2002 | Bryant et al. | |
| D463,558 S | 9/2002 | Bryant et al. | |
| D463,559 S | 9/2002 | Bryant et al. | |
| 6,454,770 B1 | 9/2002 | Klaue | |
| D464,136 S | 10/2002 | Bryant et al. | |
| D464,731 S | 10/2002 | Bryant et al. | |
| 6,468,278 B1 | 10/2002 | Muckter | |
| 6,488,685 B1 | 12/2002 | Manderson | |
| D469,532 S | 1/2003 | Bryant et al. | |
| D469,533 S | 1/2003 | Bryant et al. | |
| D469,534 S | 1/2003 | Bryant et al. | |
| 6,503,252 B2 | 1/2003 | Hansson | |
| 6,503,281 B1 | 1/2003 | Mallory | |
| 6,508,819 B1 | 1/2003 | Orbay | |
| D469,874 S | 2/2003 | Bryant et al. | |
| D469,875 S | 2/2003 | Bryant et al. | |
| D470,588 S | 2/2003 | Bryant et al. | |
| 6,527,776 B1 | 3/2003 | Michelson | |
| 6,533,789 B1 * | 3/2003 | Hall et al. | 606/281 |
| 6,602,256 B1 | 8/2003 | Hayes | |
| 6,605,090 B1 | 8/2003 | Trieu et al. | |
| D479,331 S | 9/2003 | Pike et al. | |
| D480,141 S | 9/2003 | Benirschke et al. | |
| 6,623,486 B1 * | 9/2003 | Weaver et al. | 606/281 |
| 6,669,701 B2 | 12/2003 | Steiner et al. | |
| 6,730,091 B1 | 5/2004 | Pfefferle et al. | |
| 6,767,351 B2 | 7/2004 | Orbay et al. | |
| 6,835,197 B2 * | 12/2004 | Roth et al. | 606/62 |
| 6,955,677 B2 | 10/2005 | Dahners | |
| 7,001,388 B2 | 2/2006 | Orbay et al. | |
| 7,169,149 B1 * | 1/2007 | Hajianpour | 606/54 |
| 7,179,260 B2 | 2/2007 | Gerlach et al. | |
| 7,316,687 B2 | 1/2008 | Aikins et al. | |
| 7,527,639 B2 | 5/2009 | Orbay et al. | |
| 7,951,176 B2 | 5/2011 | Grady et al. | |
| 8,092,505 B2 * | 1/2012 | Sommers | 606/329 |
| 2001/0000186 A1 | 4/2001 | Bramlet et al. | |
| 2001/0011172 A1 | 8/2001 | Orbay et al. | |
| 2001/0012940 A1 | 8/2001 | Tunc | |
| 2002/0013587 A1 | 1/2002 | Winquist et al. | |
| 2002/0032446 A1 | 3/2002 | Orbay | |
| 2002/0045901 A1 | 4/2002 | Wagner et al. | |
| 2002/0049445 A1 | 4/2002 | Hall, IV et al. | |
| 2002/0062127 A1 | 5/2002 | Schumacher et al. | |
| 2002/0065516 A1 | 5/2002 | Winquist et al. | |
| 2002/0128654 A1 | 9/2002 | Steger et al. | |
| 2002/0143337 A1 | 10/2002 | Orbay et al. | |
| 2002/0143338 A1 | 10/2002 | Orbay et al. | |
| 2002/0156474 A1 | 10/2002 | Wack et al. | |
| 2002/0183752 A1 | 12/2002 | Steiner et al. | |
| 2002/0183753 A1 | 12/2002 | Manderson | |
| 2003/0040748 A1 | 2/2003 | Aikins et al. | |
| 2003/0055435 A1 | 3/2003 | Barrick | |
| 2003/0060827 A1 | 3/2003 | Coughln | |
| 2003/0083660 A1 | 5/2003 | Orbay | |
| 2003/0083661 A1 | 5/2003 | Orbay et al. | |
| 2003/0105461 A1 | 6/2003 | Putnam | |
| 2003/0125738 A1 | 7/2003 | Khanna | |
| 2003/0135212 A1 | 7/2003 | Chow | |
| 2003/0135216 A1 | 7/2003 | Sevrain | |
| 2004/0030339 A1 * | 2/2004 | Wack et al. | 606/69 |
| 2004/0049193 A1 | 3/2004 | Capanni | |
| 2004/0097937 A1 | 5/2004 | Pike et al. | |
| 2004/0254579 A1 | 12/2004 | Buhren et al. | |
| 2005/0165400 A1 | 7/2005 | Fernandez | |
| 2005/0171544 A1 | 8/2005 | Falkner, Jr. | |
| 2005/0216001 A1 | 9/2005 | David | |
| 2005/0277937 A1 | 12/2005 | Leung et al. | |
| 2006/0264946 A1 | 11/2006 | Young | |
| 2011/0046681 A1 | 2/2011 | Prandi et al. | |
| 2011/0087229 A1 | 4/2011 | Kubiak et al. | |
| 2011/0106081 A1 | 5/2011 | Graham et al. | |
| 2012/0245642 A1 | 9/2012 | Giannoudis et al. | |

FOREIGN PATENT DOCUMENTS

| | | |
|---|---|---|
| DE | 3722852 | 1/1989 |
| DE | 3743638 | 7/1989 |
| DE | 4004941 | 8/1990 |
| DE | 4201531 | 7/1993 |
| DE | 4341980 | 6/1995 |
| DE | 4343117 | 6/1995 |
| DE | 4438264 | 3/1996 |
| DE | 19636733 | 4/1997 |
| DE | 9321544 | 9/1999 |
| DE | 19858889 | 6/2000 |
| DE | 10015734 | 9/2001 |
| DE | 10125092 | 12/2001 |
| EP | 0180532 | 5/1986 |
| EP | 0207884 | 1/1987 |
| EP | 0251583 | 1/1988 |
| EP | 0274713 | 7/1988 |
| EP | 0290138 | 11/1988 |
| EP | 0291632 | 11/1988 |
| EP | 0299160 | 1/1989 |
| EP | 0337288 | 10/1989 |
| EP | 0381462 | 8/1990 |
| EP | 0382256 | 8/1990 |
| EP | 0471418 | 2/1992 |
| EP | 0532421 | 3/1993 |
| EP | 0546460 | 6/1993 |
| EP | 0649635 | 4/1995 |
| EP | 0668059 | 8/1995 |
| EP | 0760231 | 3/1997 |
| EP | 1132052 | 3/2000 |
| EP | 1468655 | 10/2004 |
| FR | 742618 | 3/1933 |
| FR | 2233973 | 1/1975 |
| FR | 2405062 | 5/1979 |
| FR | 2405705 | 5/1979 |
| FR | 2405706 | 5/1979 |
| FR | 2496429 | 6/1982 |
| FR | 2606268 | 5/1988 |
| FR | 2622431 | 5/1989 |
| FR | 2650500 | 2/1991 |
| FR | 2671966 | 7/1992 |
| FR | 2677876 | 12/1992 |
| FR | 2706763 | 12/1994 |
| FR | 2757370 | 6/1998 |

(56) References Cited

FOREIGN PATENT DOCUMENTS

| | | |
|---|---|---|
| FR | 2802082 | 6/2001 |
| GB | 2017502 | 10/1979 |
| GB | 2090745 | 7/1982 |
| GB | 2245498 | 1/1992 |
| GB | 2257913 | 1/1993 |
| JP | 2121652 | 5/1990 |
| JP | 3158150 | 7/1991 |
| JP | 4138152 | 5/1992 |
| JP | 6125918 | 5/1994 |
| JP | 6245941 | 9/1994 |
| JP | 898846 | 4/1996 |
| JP | 8126650 | 5/1996 |
| JP | 8257034 | 10/1996 |
| JP | 8266562 | 10/1996 |
| JP | 9108237 | 4/1997 |
| JP | 11/76259 | 3/1999 |
| JP | 11/276501 | 10/1999 |
| JP | 11/299804 | 11/1999 |
| JP | 11/318930 | 11/1999 |
| JP | 2000/000247 | 1/2000 |
| JP | 2000-152944 | 6/2000 |
| JP | 2001/149379 | 6/2001 |
| JP | 2001/161704 | 6/2001 |
| JP | 2001-514039 | 9/2001 |
| JP | 2002/095673 | 4/2002 |
| JP | 2002/345836 | 12/2002 |
| JP | 2003/024344 | 1/2003 |
| JP | 2003/038508 | 2/2003 |
| JP | 2003/038509 | 2/2003 |
| JP | 2003-509107 | 3/2003 |
| SU | 1279626 | 12/1986 |
| WO | WO 92/11819 | 7/1992 |
| WO | WO 93/11714 | 6/1993 |
| WO | WO 93/15678 | 8/1993 |
| WO | WO 93/22982 | 11/1993 |
| WO | WO 94/02073 | 2/1994 |
| WO | WO 95/32674 | 12/1995 |
| WO | WO 96/17556 | 6/1996 |
| WO | WO 97/08999 | 3/1997 |
| WO | WO 97/09000 | 3/1997 |
| WO | WO 98/02105 | 1/1998 |
| WO | WO 98/05263 | 2/1998 |
| WO | WO 00/53110 | 9/2000 |
| WO | WO 00/53111 | 9/2000 |
| WO | WO 01/19267 | 3/2001 |
| WO | WO 01/19268 | 3/2001 |
| WO | WO 01/89400 * 11/2001 | ............ A61B 17/86 |
| WO | WO 02/071963 | 9/2002 |
| WO | WO 03/022166 | 3/2003 |
| WO | WO 03/028567 | 4/2003 |
| WO | WO 2004043277 A1 * 5/2004 | ............ A61B 17/86 |
| WO | WO 2004/107957 | 12/2004 |
| WO | WO 2005/044121 | 5/2005 |
| WO | WO 0189400 * 11/2011 | ............ A61B 17/86 |

* cited by examiner

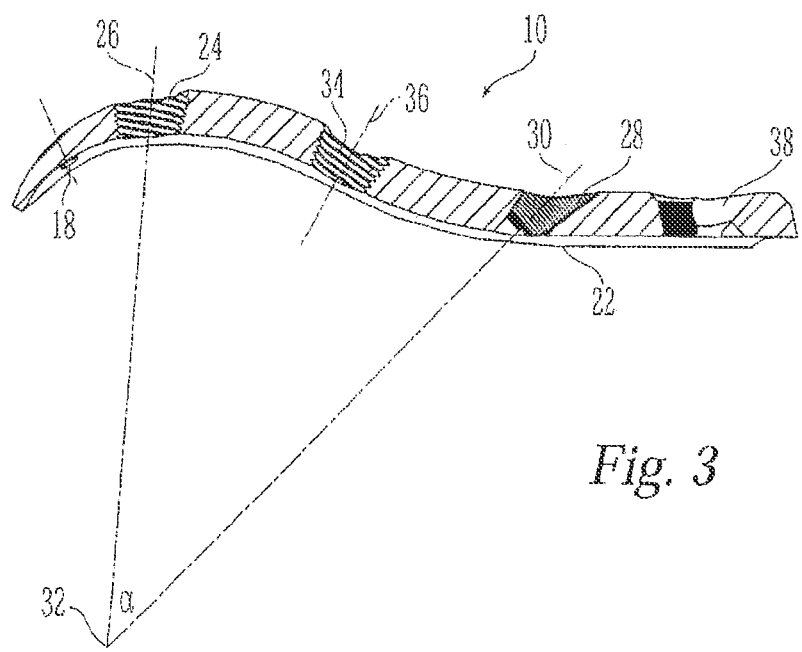
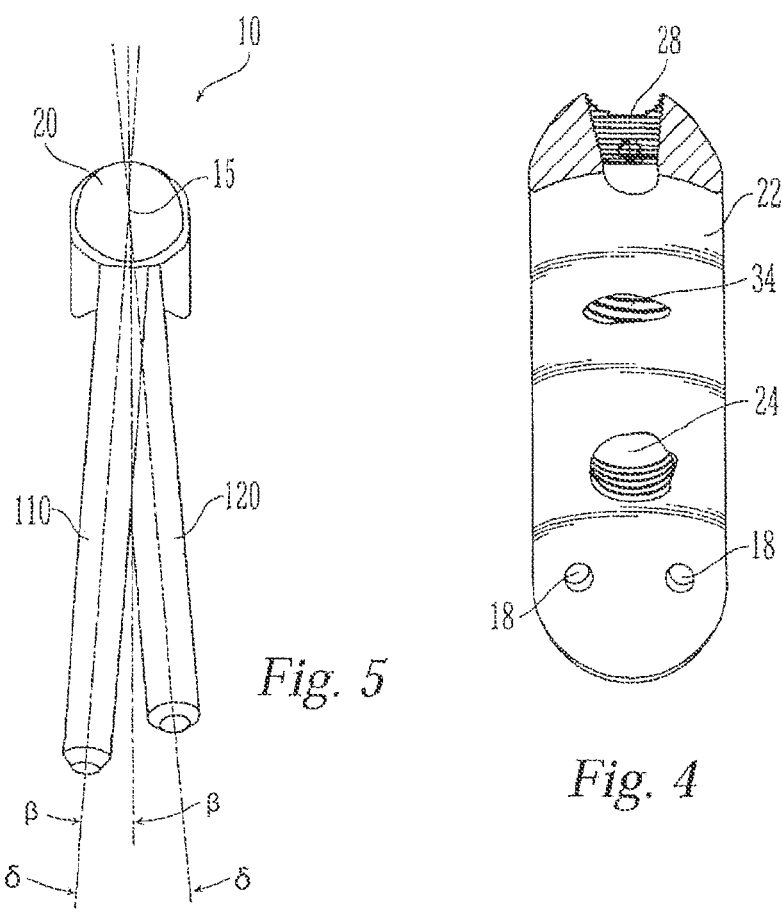
Fig. 3
Fig. 5
Fig. 4

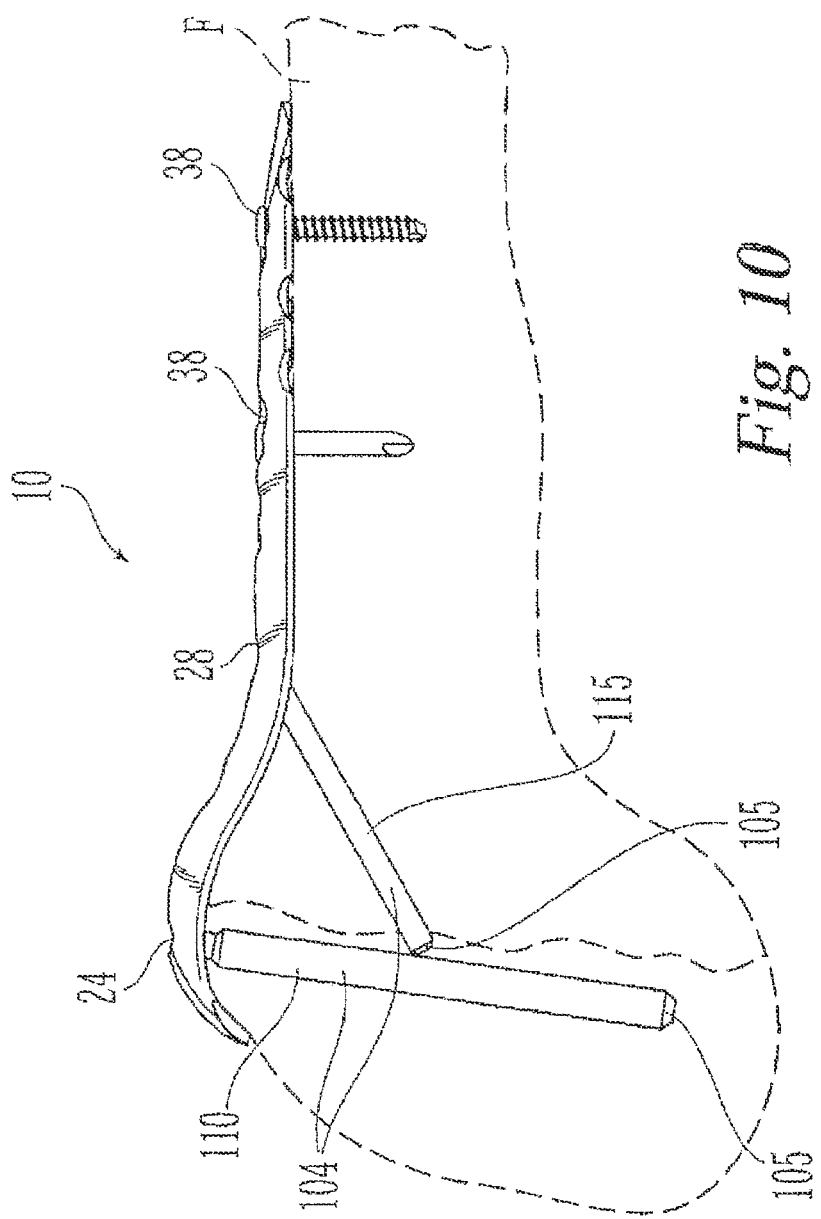

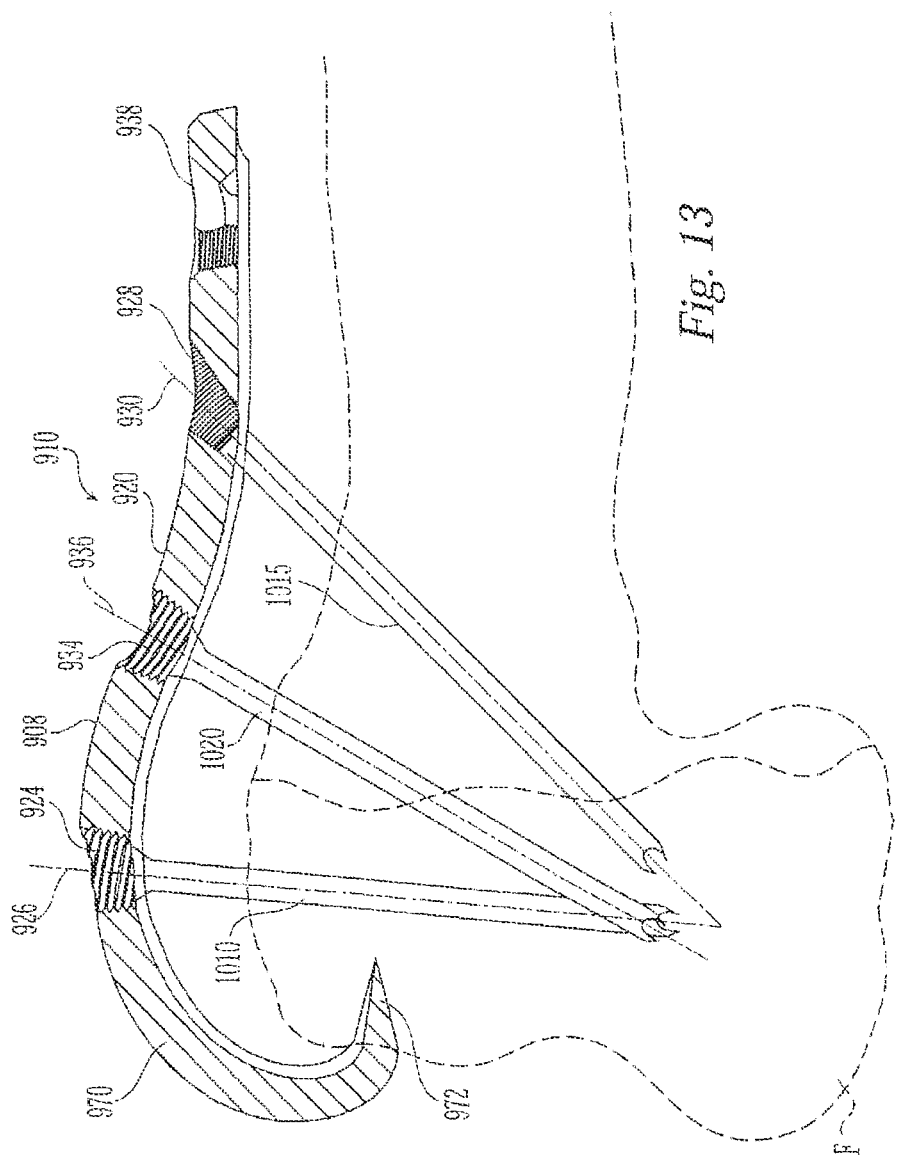

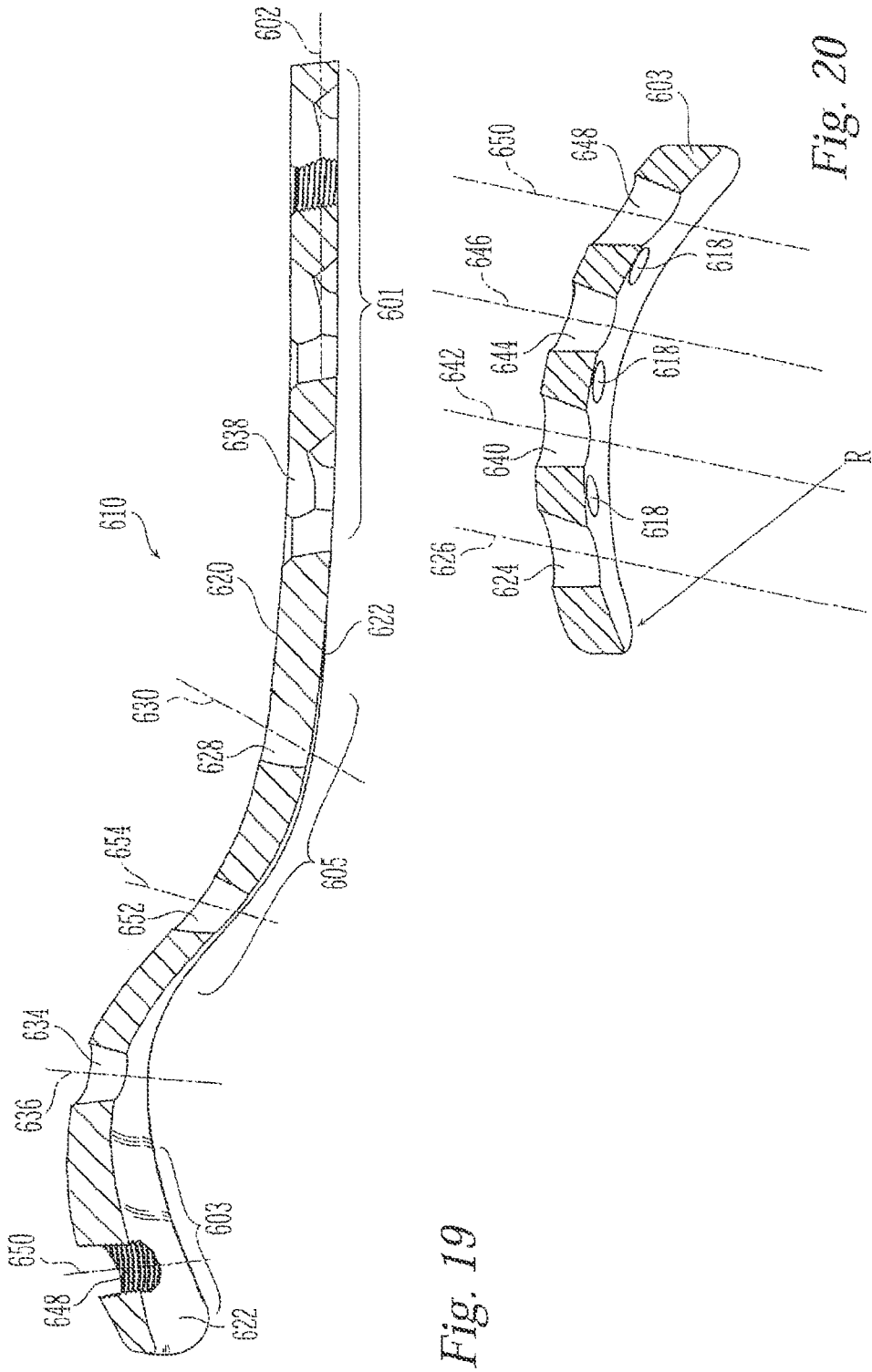

BONE PLATE

CROSS REFERENCE TO RELATED APPLICATIONS

This is a continuation application of U.S. patent application Ser. No. 13/092,625, filed on Apr. 22, 2011, which is a continuation of U.S. patent application Ser. No. 10/843,113, filed on May 11, 2004, now U.S. Pat. No. 7,951,176, which in turn claims priority to U.S. Provisional Patent Application Ser. No. 60/474,279, filed on May 30, 2003.

TECHNICAL FIELD OF THE INVENTION

The present invention relates generally to bone plates, and more specifically, to bone plates for the fixation of parts of a fractured bone, preferably long bones, including the femur and the tibia.

BACKGROUND OF THE INVENTION

A bone plate is a plate that is fastenable to the surface of a bone typically at both sides of a fracture to support and/or stabilize the fracture. Bone plates have typically been attached to the bone with bone screws that extend from the plate into the bone. In some examples, the head of the bone screw is locked to the plate (e.g., by threaded engagement between the screw head and the bone plate) and in other plates the head of the screw is free to angulate with respect to the plate, such that the screw may be placed in the bone at a surgeon-selected angle. In yet other examples, the screw head may cooperate with the bone plate to provide compression or distraction of the fracture (i.e., to push the bone fragments towards or away from one another).

When treating certain types of fractures, such as that of the proximal portion of the femur, there may be high stresses at the bone-screw and/or screw-plate interfaces. Several different types of bone plates have been developed to accommodate these high stresses. In one example known as a "blade plate," the bone plate may have a blade-shaped portion that extends approximately perpendicularly to the plate, and extends into a channel formed in the bone through the fracture site. In another example, a lag screw may extend from a barrel portion of the plate and through the fracture site. With both of these systems, however, a large amount of bone must be removed to accommodate the blade or barrel. In addition, the surgical procedures are technically difficult, as the bone must be removed with precision in order to allow proper positioning of the bone plate on the bone.

SUMMARY OF THE INVENTION

The present invention in one embodiment is directed to a bone plate having a longitudinal axis and comprising an upper surface, a lower surface, a first hole for engaging an end portion of a first bone anchor, the first hole being configured and adapted to fix a shaft of the first bone anchor along a first axis, and a second hole spaced apart from the first hole along the longitudinal axis, the second hole for engaging an end portion of a second bone anchor and configured and adapted to fix a shaft of the second bone anchor along a second axis. The first hole and the second hole may be configured such that the first axis and the second axis define a single plane and intersect at a point below the lower surface of the bone plate. The bone plate may further include a third hole for engaging an end portion of a third bone anchor such that a shaft of the third bone anchor is fixed along a third axis, wherein the third hole preferably is located between the first and second holes and the third axis lies at an angle relative to the plane defined by the first and second axes. The first, second, and third holes may be positioned along the longitudinal axis of the bone plate. A shaft of the first bone anchor may contact or nearly contact a shaft of a second bone anchor. The first, second and third bone anchors may be bone screws, blades, or other anchors known to one of ordinary skill in the art for engaging bone.

According to one illustrative embodiment, the plane defined by the first and second axes may lay at an angle relative to a plane bisecting the bone plate along the longitudinal axis and or the central axis. Additionally or alternatively, the first and second holes may be configured such that the first and second axes define an acute angle at the point of intersection.

Preferably, at least one of the first and second holes may be threaded to engage threads on the end portion of a bone screw, or alternatively, at least one of the first and second holes may be dimensioned and configured for an end of a bone screw to be press fit therein. Preferably, at least one of the first and second holes are configured so that the bone anchor will be fixed to the bone plate when engaged therewith at a predetermined angle with respect to the plane formed by the lower surface of the bone plate at the location of the respective hole. The angle formed between the lower surface of the bone plate and the axis of one of the bone anchors may be approximately perpendicular, and optionally the angle between the axis of the second bone anchor and the lower surface forms an acute angle. More preferably, the angles of the axes of the bone anchors which are predetermined by the nature of the bone anchors engagement with the respective hole, are such that the bone anchors will form a truss formation. More preferably, at least one or more holes in the bone plate are oriented such that bone anchors engaged in the bone plate are fixed, and at least a first bone anchor, preferably its tip, contacts at least a second bone anchor along the length of the second bone anchor.

The bone plate may also include at least one combination hole for receiving a bone screw, the combination hole having a first portion and a second portion, wherein the first portion defines a substantially circular outer periphery defining a first center point, and the second portion defines an elongated outer periphery that defines a second center point. The elongated outer periphery may be elongated in a direction substantially parallel to the longitudinal axis of the plate, and the second portion may overlap the first portion. A plurality of threads may be disposed on the first portion of the combination hole for threadably engaging the head of a bone screw. The second portion of the combination hole may be configured and dimensioned to engage a substantially spherical head of a bone screw.

The present invention in another embodiment is also directed to bone plating systems including a bone plate and various combinations of bone anchors (e.g., bone screws, blades, etc.). The bone plate may also include a first end and a second end, in which the first end is configured for following the contour of the bone. The first end may include a hook configured to engage bone tissue. The hook may include an edge located below the lower surface of the bone plate for penetrating into bone tissue. The edge of the hook may be formed by two spaced apart talons.

The bone plate may also comprise a first section having a first longitudinal axis, a second section defining a second longitudinal axis, and a transition section connecting the first section to the second section such that an included angle is defined between the first longitudinal axis and the second longitudinal axis. The included angle between the first and second longitudinal axes may be obtuse, acute or approximately right angled. The first section, the second section and the transition sections may be integral with one another made from a single piece of material, or alternatively joined together by techniques known to one of ordinary skill in the art. Additionally, the first section may be longer than the second section, and the transition section may connect the first section to the second section such that the bone plate is substantially L-shaped or T-shaped. The transition section may also be bent or twisted to connect the first section to the second section which may locate the second section in a plane different from that of the first section. The upper surface of the transition section may be substantially S-shaped. The lower surface of the first, second and transition sections may also define radius of curvature along their longitudinal axes.

The present invention is also generally directed to a method of using a bone plate according to the present invention for reducing bone fractures. The method comprises the steps of affixing an embodiment of a bone plate according to the present invention across the gap of a fracture zone and engaging the threaded head of a bone screw in a threaded hole of the bone plate so as form a threaded locked engagement. The threaded hole is configured for threaded locked engagement with the threaded head of the bone screw. The threaded hole may fix the bone screw along an axis at such an angle relative to the lower surface of the bone plate such that upon the threaded locked engagement of the bone screw with the bone plate, the gap of the bone fracture is reduced.

BRIEF DESCRIPTION OF THE DRAWINGS

To facilitate an understanding of the characteristics, structure and operation of the invention, preferred exemplary features of the invention are described in the accompanying discussion, it being understood that the invention in its various embodiments is not limited to the preferred examples illustrated and, wherein similar reference characters denote similar elements throughout the several views or embodiments, and wherein:

FIG. 3 is a cross-sectional view of a portion of the bone plate of FIG. 1; taken along line of FIG. 2;

FIG. 4 is a perspective, partial view of the lower surface of the bone plate of FIG. 1, with a portion of the bone plate shown in cross-section;

FIG. 5 is a front view of the bone plate of FIG. 1;

FIG. 10 is a plan view of the bone plate of FIG. 1 having an alternate bone screw configuration

FIG. 13 is a cross-sectional view of another illustrative embodiment of a bone plate according to the present invention;

FIG. 19 is a cross-sectional, partial view of the bone plate of FIG. 18, taken along the line XIX-XIX of FIG. 18;

FIG. 20 is a cross-section, partial view of the bone plate of FIG. 18, taken along the line XX-XX of FIG. 18;

DETAILED DESCRIPTION OF THE PREFERRED EMBODIMENTS

Figure 1:
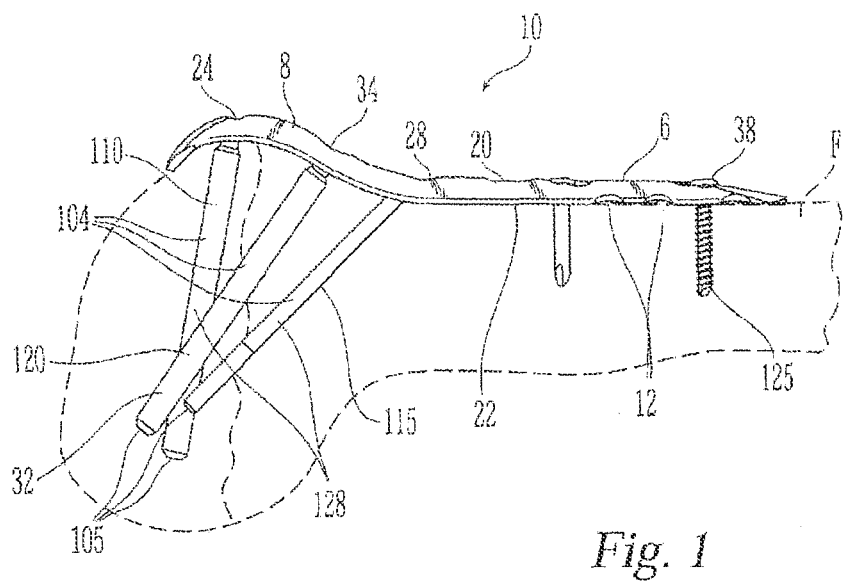
FIG. 1 is a side view of a first illustrative embodiment of a bone plate according to the present invention, shown attached to a proximal portion of a fractured femur by a plurality of bone screws.

For convenience, the same or equivalent elements in various embodiments of the bone plate illustrated in the drawings have been identified with the same reference numerals. Further, in the description that follows, any reference to either orientation or direction is intended primarily for the convenience of description and is not intended in any way to limit the scope of the present invention thereto.

A first illustrative embodiment of a bone plate 10 is shown in FIG. 1. The bone plate 10 shown in FIG. 1 is dimensioned and configured for internal fixation of the proximal portion of a fractured femur F. One of ordinary skill in the art will know and appreciate, however, that the principles of the present invention may be applied to bone plates for fixation of other bones of humans and/or animals, for example long bones, and for different parts of long bones (e.g., the proximal tibia, the distal femur, etc.).

Figure 2:
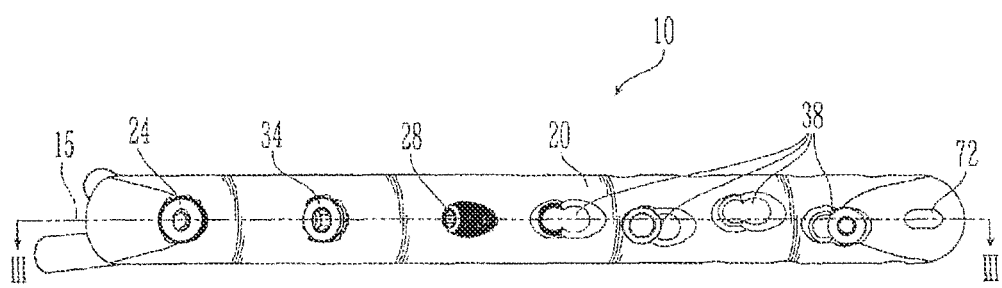
FIG. 2 is a top view of a portion of the bone plate of FIG. 1.

As shown in FIGS. 1 and 2, bone plate 10 has a longitudinal axis 15, and includes an upper surface 20 and a lower surface 22. Bone plate 10 may be constructed from biocompatible materials such as, for example, titanium, alloys of titanium, stainless steel, resorbable materials, and allograft, although one of ordinary skill in the art will know and appreciate that any biocompatible material may be used. As will be discussed in greater detail below and shown generally in FIGS. 1 and 3, bone plate 10 is configured to receive a plurality of bone anchors 110, 115, 120, 125. Bone anchors 110, 115, 120 and 125 are shown in FIG. 1 as bone screws, however other types of bone anchors known to one of ordinary skill in the art, such as blades, nails, pins, etc, may be used. The engagement of the bone plate 10 and screws 110, 115 may result in a truss formation 128 for effectively anchoring bone plate 10 to the proximal portion of a fractured femur, or other bone. Lower surface 22 may contact the bone F directly, as shown, or alternatively, may be held at a distance from the bone surface to facilitate increased flow of blood over the fracture zone.

Now referring to FIG. 3, a cross-sectional view of bone plate 10 is shown. Bone plate 10 may include a first hole 24 and a second hole 28. First hole 24 may define a central axis 26 along which the shaft portion of a first bone anchor would extend, and second hole 28 may define a central axis 30 along which the shaft of a second bone anchor would extend. First and second holes 24 and 28 may be configured such that central axes 26, 30 define a single plane and intersect in that plane at a point 32 below the lower surface 22. The intersection of central axes 26, 30 may define an angle α, which is preferably an acute angle, and more preferably, between about 3° and about 60°. The central axis 26 of the first hole 24 may be substantially perpendicular to the lower surface 22 of the bone plate 10 or to the exterior surface of the bone F into which it is inserted. For example, central axis 26 may preferably be oriented at about a 95° with respect to the lower surface 22 of the bone plate 10. The central axis 30 of the second hole 28 may be at an acute angle with respect to the lower surface 22 of the bone plate 10 or to the exterior of the bone F in which it is inserted. Bone plate 10 may also include at least two guide holes 18 as shown in FIGS. 3 and 4 for receiving and guiding a wire.

First and second holes 24, 28 may each be configured for engaging the head of a bone anchor. More preferably, first and second holes 24, 28 may be configured for fixing and locking with the bone anchor and more preferably for fixing the bone anchor in a fixed, predetermined orientation with respect to the lower surface 22 of the bone plate 10 or the exterior surface of the bone in to which it is inserted, for example, by threaded engagement, interference or press fitting, or any other form of joining the plate 10 with the screw heads known to one of ordinary skill in the art. The bone anchor is fixed to the plate such that its shaft or shank would extend along the central axes 26, 30 of the holes 24, 28 in the bone plate 10. In the illustrative embodiment shown in FIG. 3, holes 24, 28 are threaded for respective engagement with bone anchors having threaded heads.

Figure 6:
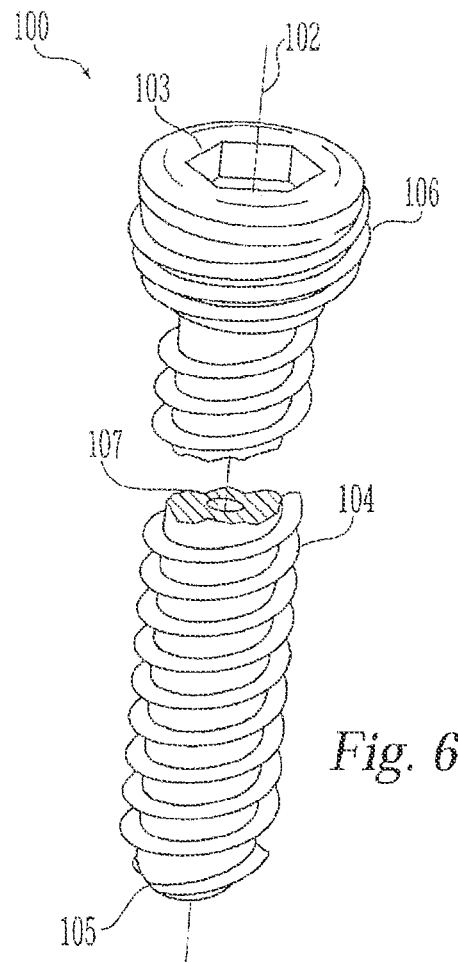
FIG. 6 is a perspective view of a bone screw having a threaded head for use with a bone plate according to one embodiment of the present invention.
Figure 7:
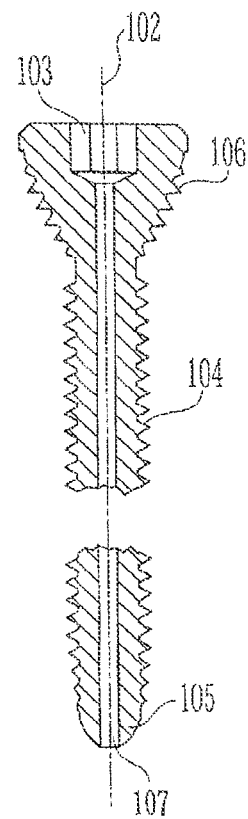
FIG. 7 is a cross-sectional view of the bone screw of FIG. 6.

An example of such a bone anchor is shown in FIGS. 6 and 7. Bone screw 100 defines a central axis 102, a shaft in the form of a threaded shank 104 with tip 105, and a threaded head 106. Bone screw 100 may be constructed from, for example, titanium, alloys of titanium, stainless steel, resorbable materials such as polymers, allograft or other biocompatible materials known in the art. Bone screw 100 is preferably compatible with the bone plate 10 in terms of composition and strength. Bone screw 100 may be cannulated having a through bore or channel 107 extending from the upper surface 103 head 106 to the tip 105, as seen in FIG. 7, for introducing instruments, for example, a guide wire into the fracture zone.

Figures 8, 9:
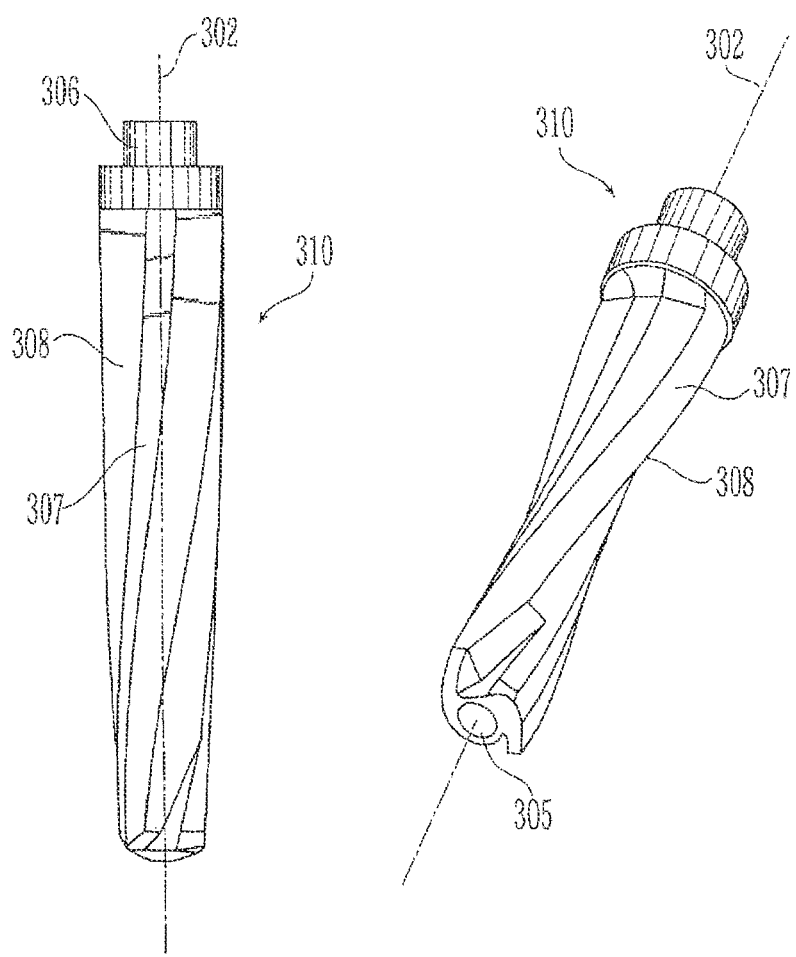
FIG. 8 is a plan view of a spiral blade for use with a bone plate according to one embodiment of the present invention.
FIG. 9 is a perspective view of the spiral blade of FIG. 8.

Another bone anchor that may be in a fixed and locked engagement with first and second holes 24, 28 is the spiral blade 310 shown in FIGS. 8 and 9. Blade 310 defines a longitudinal axis 302 and has a proximal end 306, a distal end 304 and an external surface 308 in the form of spiral flutes 307, although other configurations are possible. The spiral blade 310 may be cannulated with a central channel 305, as shown, or may be substantially solid. The proximal end 306 of blade 310 may be engaged in first or second hole 24, 28 by press-fitting or interference fitting, although the present invention is not limited to any specific type of junction between the bone plate and the bone anchors.

Referring back to FIG. 3, threaded holes 24, 28 may be separately engaged by the threaded heads 106 of the bone screw 100 to form a locking threaded engagement between the plate and the threaded head 106, thereby aligning shanks 104, and central axis 102, along central axes 26, 30. The internal thread pattern of threaded holes 24, 28 and the matching thread pattern of threaded head 106 may preferably have a screw thread profile having a 60° thread angle, but other thread patterns are possible. The threaded engagement of the bone plate 10 and the threaded head 106 prevents movement of bone plate with respect to bone screws 100 engaged with threaded holes 24, 28, and locks the angular position of central axes 102 with respect to the plate 10 and each other. With threaded shanks 104 of the bone screws anchored to the fractured bone and the threaded heads 106 lockingly engaged with the threaded holes 24, 28, bone plate 10 is anchored to the bone. Depending upon the depth at which the threaded shank 104 is anchored into the bone, the lower surface 22 of bone plate 10 may directly contact the bone surface, or alternatively, may be affixed and spaced at a distance from the bone surface. In addition, wherein the shank 104 is of sufficient length so as to span across the gap of the fracture zone between the two fractured segments of bone F, either of the threaded holes 24, 28 and their central axes 26, 30 may align the shank 104 at such an angle with respect to the plate 10 so as to reduce the gap of the fracture zone upon locking of the threaded head 106 in the threaded hole 24, 28.

Referring again to FIGS. 1 and 3, because of the configuration of threaded holes 24, 28, in which their central axes 26, 30 intersect at a point 32 below the lower surface 22 of bone plate 10, the threaded engagement of bone screws 110, 115 with threaded holes 24, 28 form a truss 128 beneath the bone surface. The truss formation serves to increase the stability of the anchorage of bone plate 10 to the fractured bone. Additionally, the truss 128 serves to more evenly distribute loads and stresses throughout the bone plate 10 and the anchoring bone screws 110, 115. These stresses would otherwise be concentrated in the engagement between the threaded heads 106 of the bone screws 110, 115 and the bone plate 10. As shown in FIG. 1, with bone screws 110, 115 engaged with threaded holes 24, 28, bone screws 110, 115 may contact one another at or near the point of intersection 32 below the bone surface F. More preferably, the tip 105 of the second bone screw 115 may contact the first bone screw 110 at the tip 105 of the first bone screw 110, as generally shown in FIG. 1 or at another location along the shank 104 of the first bone screw 110, as shown in FIG. 10. Alternatively, the bone screws 110, 115 may not contact one another; however their central axes 102 may intersect to define a plane and thereby operably associate the bone screws 110, 115 with one another to more evenly distribute the loads and stresses experienced at the threaded screw head 106 to plate 10 interface.

As is shown in FIGS. 3 and 4, threaded holes 24, 28 may be conically tapered in a direction from the upper surface 20 to the lower surface 22 of bone plate 10. This tapering of the holes 24, 28 may facilitate alignment between the threads of holes 24, 28 and the threads on the heads 106 of bone screws 110, 115. Alternatively, threaded holes 24, 28 may be substantially cylindrical, partially spherical or other shapes known in the art. As is more clearly shown in FIG. 5, the central axes 26, 30 of threaded holes 24, 28 may define a plane that intersects and lies at an angle β relative to a plane that substantially bisects the bone plate 10 and includes the longitudinal axis 15. According to one preferred embodiment, the angle β may range from 0° to about 60°, or range to about 15°, or from about 3° to about 6°, however other angles are possible.

As shown in FIGS. 2 and 3, bone plate 10 may include a third hole 34 defining a central axis 36 for engaging the head of a third bone anchor, shown for illustrative purposes in FIGS. 1 and 5 as bone screw 120. Third hole 34 may be similarly configured as threaded holes 26, 28 so as to include a thread for threaded engagement with the threaded head of bone screw 120. Third threaded hole 34 may be conically tapered in the direction from the upper surface 20 to lower surface 22 of bone plate 10, or alternatively, threaded hole 34 may be substantially cylindrical, partially spherical or other shapes known in the art. Third threaded hole 34 may be located between threaded holes 24, 28. Referring specifically to FIG. 5, the central axis 36 of the third threaded hole 34 may intersect and lay at an angle δ relative to the plane defined by the central axes 26, 30 of the first and second threaded holes 24, 28. Angle δ may range from about 0° to about 15°, or from about 5° to about 8°, although other angles are possible. Referring to FIG. 2, threaded holes 24, 28, 34 may be located on and spaced relative to one another along longitudinal axis 15.

The central axis 36 of the third hole 34 may be configured to intersect the axis 26 of the first hole 24, and in addition or alternatively the central axis 36 may be configured to intersect the central axis 30 of the second bore hole 28. The third bone anchor 120 may contact the first bone screw 110 at the tip 105 of the bone screw 110 or at another location along the shaft 104 of the first bone screw 110. Alternatively, or in addition there to, the third screw 120 may contact the second bone screw 115 at its tip 105, or at some other location along the shank 104 of the second bone screw 115. In one embodiment, the third bone screw may contact both the first and second bone screw 110, 115, along their respective lengths, and all three bone screws may contact each other at their respective tips 105.

Figure 28:
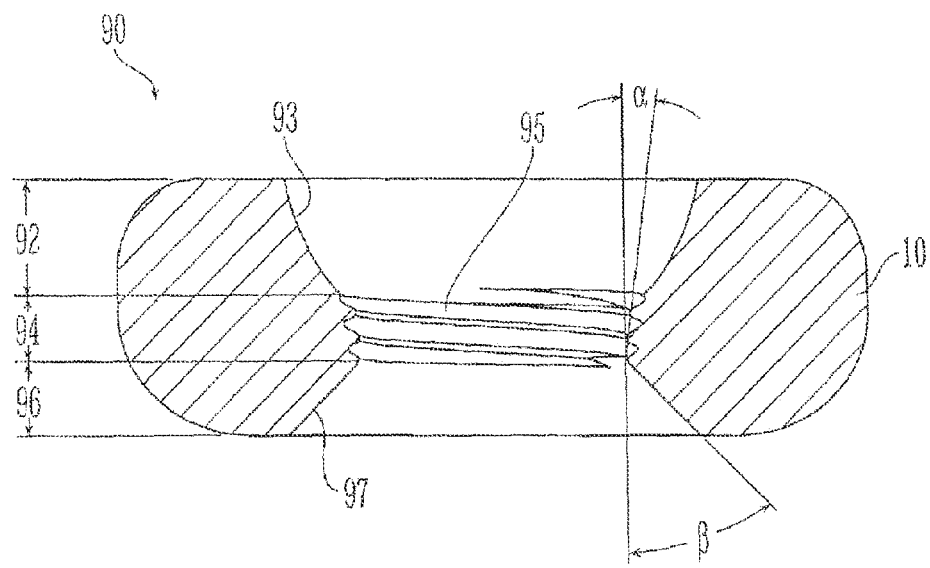
FIG. 28 is a cross-sectional view of one type of partially threaded bone plate hole, according to one embodiment of the present invention.

Reference is now made to FIG. 28. In another embodiment, in lieu of, or in addition to, having any of the afore-described holes, the bone plate 10 may have a partially threaded hole 90. The hole 90 may extend from the upper surface 20 to the lower surface 22 of the bone plate 10. The diameters of the hole 90 at its uppermost surface and at its lower most surface may be equal or close to equal to each other. The hole may be widest at the uppermost surface 20 and lowermost surface 22 of the plate 10.

As shown in 28, the hole 90 may have three regions: an upper region 92, a middle region 94, and a lower region 96. The upper region 92 of the hole 90 may have an unthreaded inner surface 93 which, is preferably smooth, although texturing may be provided. In a preferred embodiment, the upper region 92 may have a curved inward taper, preferably concave, more preferably spherical, from the top surface of the plate 10 to where the upper region 92 of the hole 90 meets the middle region 94. The upper region 92 of the hole 90 is preferably narrowest where it meets the middle region 94. In a preferred embodiment, the upper region may comprise about 25% to about 35% of the thickness of the plate 10. In a preferred embodiment, the diameter of the upper region 92, at the region's broadest point, may be about 6 mm and, at the region's narrowest point, may be about 4 mm.

The middle region 94 of the hole 90 may have a threaded inner surface 95. The threaded inner surface 95 may, in a direction from the upper surface to the lower surface of the plate 10, have a conical inward taper. In a preferred embodiment, the threaded inner surface 95 may taper at an angle α of approximately 5° to 15°, and preferably approximately 10°. The middle region 94 may be the narrowest region (i.e., smallest-diameter region) of the hole 90. In a preferred embodiment, the middle region 94 may comprise about 40% to 50% of the thickness of the plate 10. In a preferred embodiment, the diameter of the middle region 94 may vary only slightly (due to the relatively shallow conical taper) and may be about 4 mm. The diameter or taper of the middle region 94 may of course vary depending upon the size and/or taper of the screw.

The lower region 96 of the hole 90 may have an unthreaded inner surface 97 which is preferably smooth, although texturing may be provided. In a preferred embodiment, the lower region 96 may, from where it meets the middle region 94 to the lower surface of the plate, have a conical outward taper. In a preferred embodiment, the lower region 96 may taper outwardly at an angle β of approximately 35° to 55°, and preferably approximately 45°. In a preferred embodiment, the lower region 96 may comprise about 20% to 35% of the thickness of the plate. In a preferred embodiment, the diameter of the lower region 96, at the region's narrowest point, may be about 4 mm and, at the region's broadest point, may be about 6 mm.

Different types of screws may be used with the hole 90. One type of screw is a screw that has a conically-tapered threaded head. The external threads of the screw's head may mate with the internal threads 95 of the middle region 94 of the hole 90. This threaded-head screw may be inserted at only one angle (with respect to the plate), which may be fixed by the threads 95 in the plate 10.

A second type of screw that may be used with the hole 90 is a screw with a threaded shaft, but with an unthreaded head. An unthreaded-head screw may be inserted into hole 90 at any one of a number of angles. The conical outward taper (shown at surface 97) of the lower region 96 of the hole 90 provides room for the screw shaft to be inserted at an angle with respect to the center of the hole 90. Likewise, the curved inward taper of the upper region 92 of the hole 90 provides a seat (at surface 93) for the screw head to rest in when an unthreaded-head screw is inserted at an angle. A threaded-head screw may be used with a coaxial combination hole 90 in the same manner as the aforementioned unthreaded-head screw.

Although virtually any type of bone plate may benefit from coaxial combination holes 90, coaxial combination holes are particularly useful for pubic symphysis plates and other relatively small bone plates.

Referring again to FIG. 1, bone plate 10 may include a first portion 6 that is substantially planar and a second portion 8 that is substantially curved for conforming to the head of a bone, such as the proximal portion of the femur F. Bone plate 10 may alternatively be configured as a straight plate, or additionally or alternatively configured to include a flared portion in addition to a shaft portion. The lower surface 22 of first portion 6 may engage the bone surface directly, in which instance first portion 6 may include a plurality of recesses 12 spaced about the longitudinal axis 15 for minimizing contact between the bone plate 10 and the bone surface to facilitate increased blood circulation over the fracture zone. Threaded holes 24, 28 are preferably located in the second portion 8 of bone plate 10 in which the second portion 8 conforms and follows the bone head.

Figure 11A:
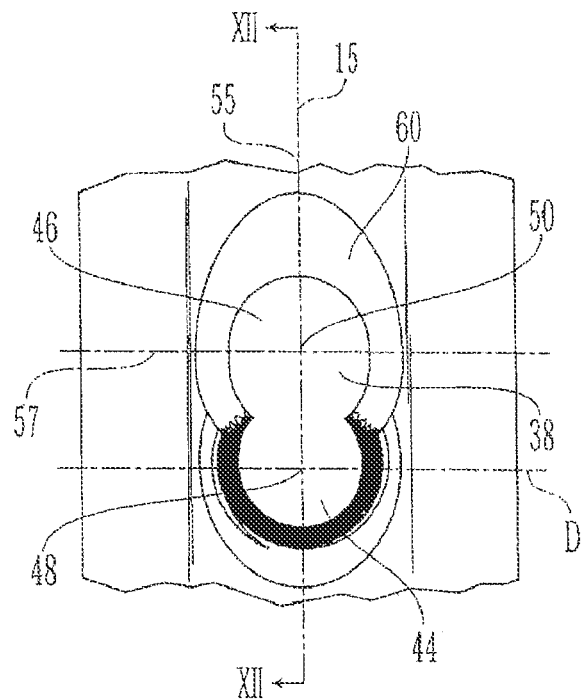
FIG. 11A is a top view of a combination hole provided in a bone plate according to one embodiment of the present invention.

Bone plate 10 may be provided with any number of holes as may be suitable for a specific surgical application. For example, as shown in FIG. 3, bone plate 10 may include one or more combination holes 38, which are substantially similar to the combination holes described in U.S. Patent Publication No. 2002/0183752 A1, incorporated herein by reference thereto. As shown in FIG. 11A, each combination hole 38 includes a first, substantially circular portion 44, and a second, elongated portion 46. The circular portion 44 and the elongated portion 46 overlap one another, and are thus in communication with one another. The outer periphery of circular portion 44 defines a first center point 48, and a diameter D. The outer periphery of elongated portion 46 defines a second center point 50. The outer periphery of elongated portion 46 also defines a major axis 55 and a minor axis 57 substantially perpendicular to the major axis 55. According to one embodiment of the invention, major axis 55 may be substantially parallel to longitudinal axis 15 of the bone plate 10. In addition, major axis 55 may lay along longitudinal axis 15 with first and second center points 48, 50 located on longitudinal axis 15, however other configurations are possible. Combination holes 38 may also be parallel but offset from longitudinal axis 15, and combination holes may be alternatively offset with respect to longitudinal axis 15.

Figure 11B:
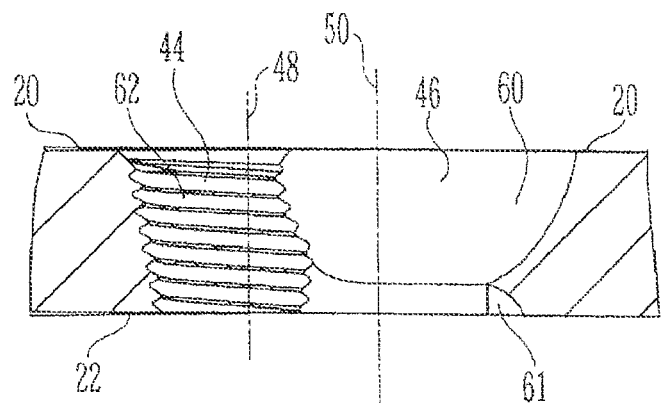
FIG. 11B is a cross-sectional view of the combination hole of FIG. 11A, taken along line XII-XII of FIG. 11A.

Elongated portion 46 may be configured and dimensioned to engage a substantially spherical screw-head of a bone screw (not shown). Additionally or alternatively, a conically shaped screw head, with or without threads, may engage the elongated portion 46. As shown in FIGS. 11A and 11B, elongated portion 46 may have a concave, substantially spherical portion or recess 60 that opens toward upper surface 20 of the bone plate 10. When the shaft of a bone screw having a spherical head is located eccentrically in elongated portion 46 (towards the right in FIG. 10), the spherical head may engage recess 60 and bias the bone plate 10 to provide compression of the bone fracture. In addition, a portion of the combination hole 38 may be concave along the lower surface 22 of the bone plate 10 to define a spherical recess 61.

Still referring to FIGS. 11A and 11B, circular portion 44 may be configured and dimensioned to engage the threaded head of a bone screw (not shown). An internal thread 62 may be provided on circular portion 44. Thread 62 may be disposed in a single plane or in several planes. The plane(s) may be parallel to upper surface 20 and/or lower surface 22. According to the illustrative embodiment shown, thread 62 extends substantially over the entire thickness of the bone plate from the upper surface 20 to lower surface 22. The internal thread 62 may be formed over an angle of approximately 190° to approximately 280°. Referring to FIG. 1, combination hole 38 is shown engaged with a bone screw 125.

Figure 12A:
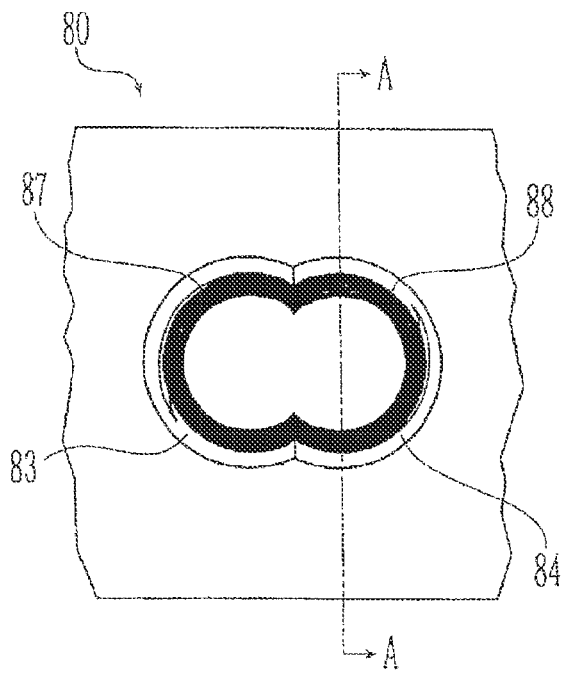
FIG. 12A is a top view of a different embodiment of a combination hole.

Reference is now made to FIG. 12A. In another embodiment, in lieu of, or in addition to, having combination hole(s) 38, the bone plate 10 may have at least one of a different type of combination hole 80. Each combination hole 80 may have two substantially circular portions 83 and 84. The circular portions 83 and 84 may overlap one another, and be in communication with one another.

Figure 12B:
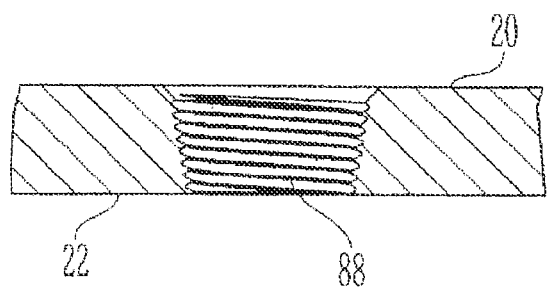
FIG. 12B is a cross-sectional view of the combination hole of FIG. 12A, taken along line A-A of FIG. 12A.

An internal thread 87 may be provided on circular portion 83. An internal thread 88 may be provided on circular portion 84. Threads 87 and 88 may extend substantially over the entire thickness of the bone plate from the upper surface 20 to the lower surface 22. FIG. 12B shows thread 88 of circular portion 84 extending the entire thickness of the bone plate. Threads 87 and 88 may be threaded in the same direction (e.g., requiring clockwise rotation for insertion of a screw with a threaded head) or in directions opposite from one another. Threads 87 and 88 may be disposed in a single plane or in several planes. The plane(s) of the threads may be parallel to upper surface 20 and/or lower surface 22 of bone plate 10, or the plane formed by the threads may be angled with respect to the upper surface 20 and/or lower surface 22. Each thread of threads 87 and 88 may be formed over an angle of approximately 190° to approximately 270°. Threads 87 and 88 may extend over the same angle or at angles different from one another. Threads 87 and 88 may have a conical inward taper. Combination hole(s) 80 may be positioned within the bone plate 10 in the same way that combination hole 38 may be positioned within the bone plate 10, as described above, or in different arrangements. In addition, combination holes 80 may be used in bone plates that also include combination holes 38, as well as any other hole described in the specification.

Shown in FIG. 13 is an alternative preferred embodiment, bone plate 910 configured substantially similar to bone plate 10. The substantial difference between bone plate 910 and bone plate 10 is that bone plate 910 may include a hook portion 970. The hook portion 970 may be attached, integral with or other wise disposed at end of the second portion 908. As was previously described with regards to second portion 8 of bone plate 10, second portion 908 may be similarly substantially curved for conforming to the head of the bone, F, for example the femoral head. The hook portion 970 includes a bone engaging edge 972 for digging or penetrating into bone tissue. More specifically, the bone plate 910 may be located along the proximal femur bone F such that second portion 908 may wrap around or conform to a portion of the greater trochanter and the hook portion 970 may engage a region of the piriformis. Bone engaging edge 972 may be configured for penetrating the bone surface to more effectively grip the bone F thereby permitting a surgeon to use bone plate 910 as a lever to resist the pull of muscle and tendons surrounding the broken segment of bone F and to properly align the bone F fragments. The depth at which the bone engaging edge 972 penetrates the bone F may be limited by the interference of the greater trochanter with the lower surface 922 of the bone plate 910. Once the bone F is properly aligned, bone screws engaged with and fixedly aligned by holes 924, 928, 934 may be inserted in the bone so as to fix bone plate 910 with respect to bone F.

Figure 14:
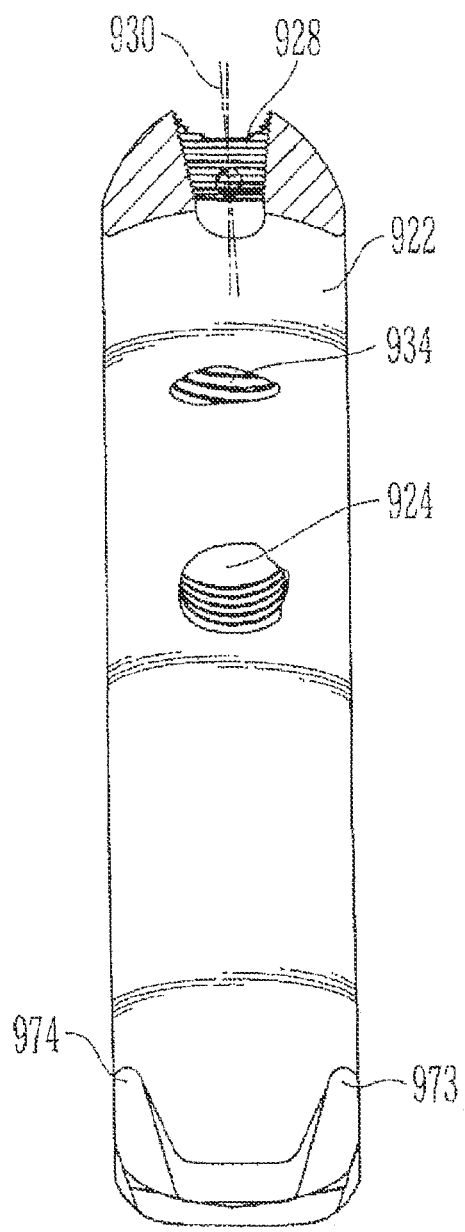
FIG. 14 is a perspective, partial view of the lower surface of the bone plate of FIG. 13, with a portion of the bone plate shown in cross-section.

Shown in FIG. 13, the hook portion 970 is configured so as to curve inward toward the first portion 906 of the bone plate 910 and terminating at a point beneath the lower surface 922 so as not to interfere with a bone anchor engaged with the first hole 924. Shown in FIG. 14, the edge 972 may be preferably formed by two spaced apart talons 973, 974 although other configuration are possible to facilitate the secure engagement of hook 972 with the bone tissue.

Figure 15:
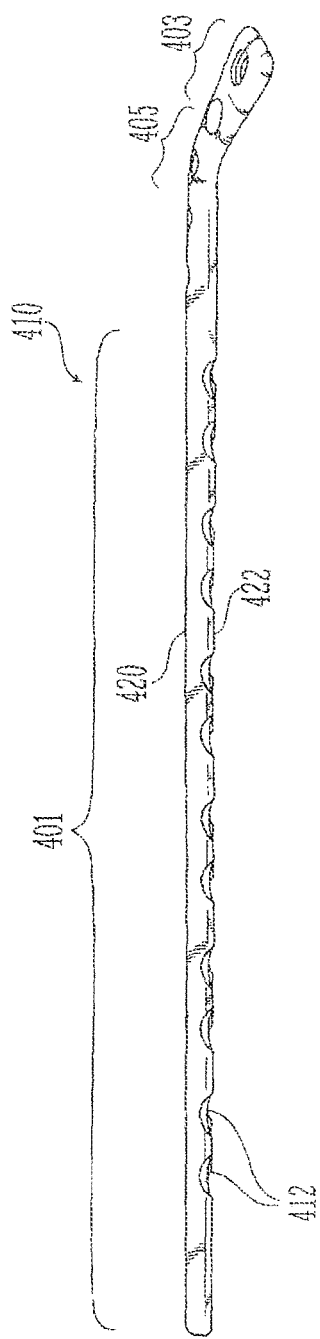
FIG. 15 is a side view of a still further illustrative embodiment of a bone plate according to the present invention.
Figure 16:
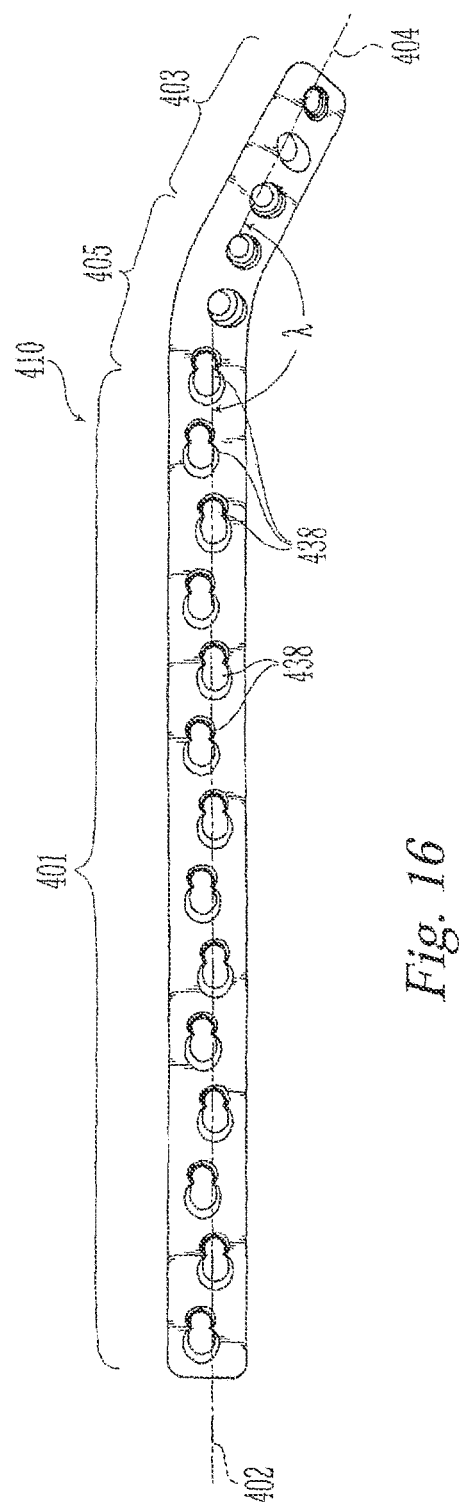
FIG. 16 is a top view of the bone plate of FIG. 15.
Figure 17:
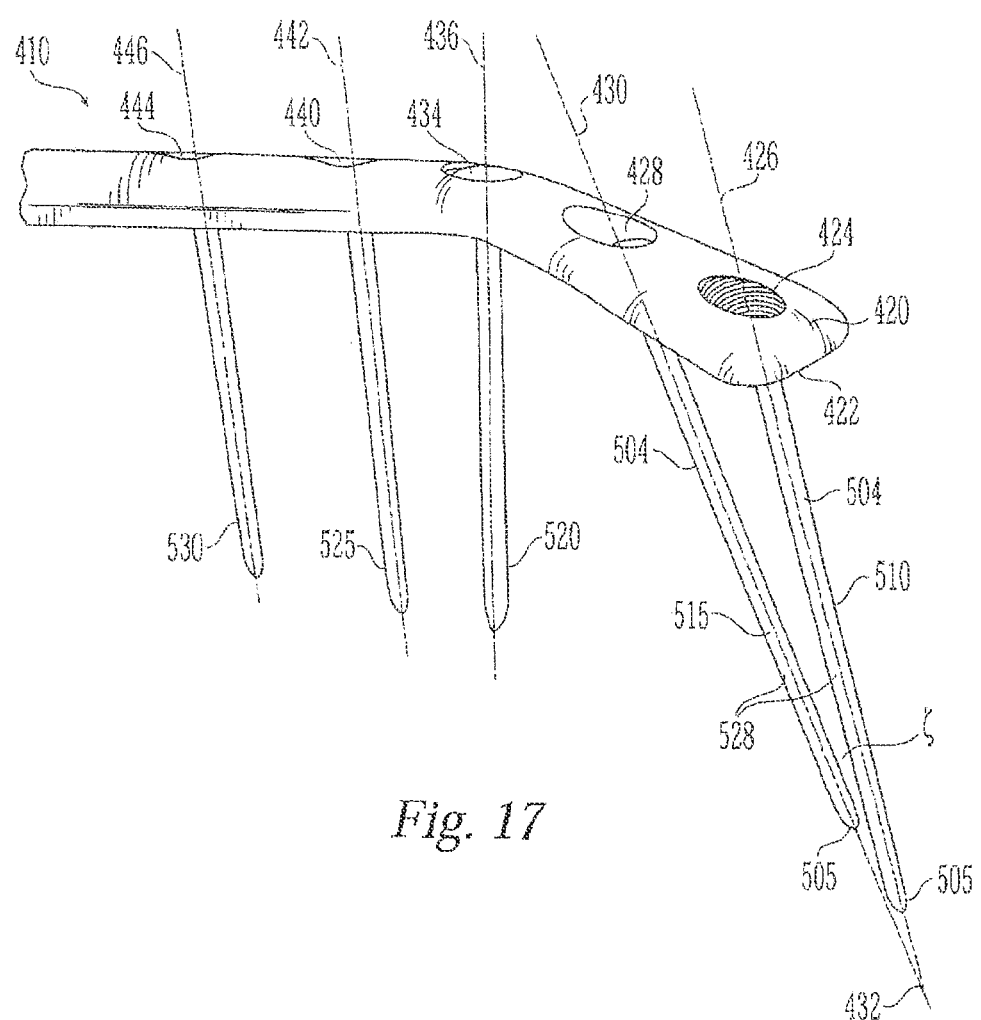
FIG. 17 is a perspective partial view of the bone plate of FIG. 15.
Figure 18:
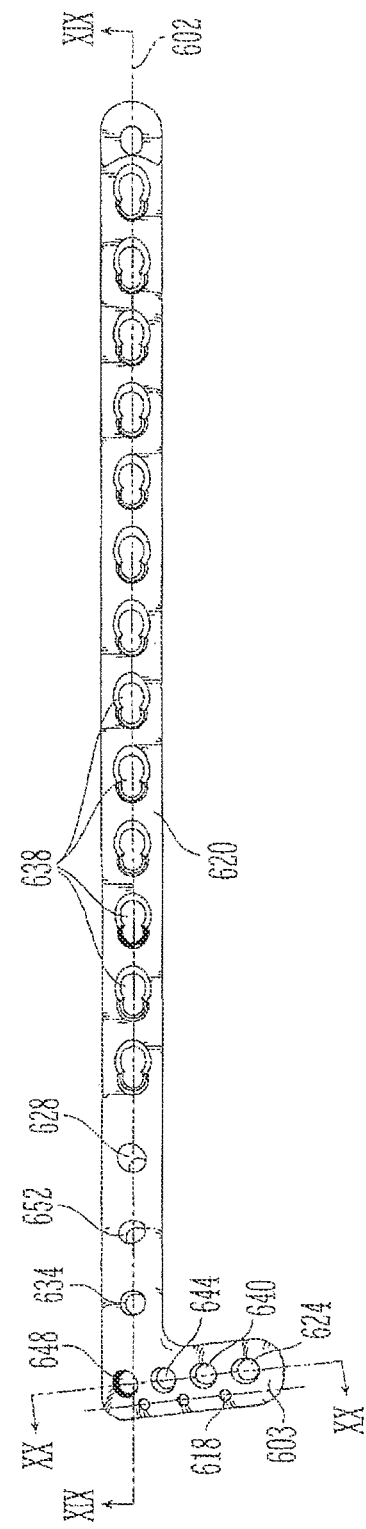
FIG. 18 is a top view of another illustrative embodiment of a bone plate according to the present invention.

Shown in FIGS. 15-27 are alternative embodiments of the bone plates configured for fixation of other long bones, for example, the tibia or humerus. Referring to FIG. 15-17, shown is an alternative embodiment, bone plate 410 which includes upper surface 420, a lower surface 422, a first section 401, which has a first longitudinal axis 402, and a second section 403, which has a second longitudinal axis 404. As with bone plate 10, the lower surface 422 of bone plate 410 may contact the surface of the bone directly, or alternatively, at least a portion of lower surface 422 may be held at a distance from the bone surface to facilitate increased flow of blood over the fracture zone. As seen in FIG. 15, recesses 412 may be provided along the lower surface 422 to facilitate the flow of blood over the fracture zone. Referring now to FIG. 18, the bone plate 410 may further include a transition section 405 connecting the first section 401 to the second section 403 in a manner such that the first longitudinal axis 402 and the second longitudinal axis 404 define an angle λ in between. The first, second, and transition sections 401, 403, 405 may be formed from a single piece of material, however other configurations are possible, for example, the pieces may be welded or otherwise joined together. In addition, first, second and transition sections 401, 403, 405 may have substantially the same width throughout the bone plate, and may be substantially parallelogram in shape. However, other configurations are possible, for example, at least one of the sections 401, 403, 405 may be flared or generally polygonal in shape.

Referring to FIG. 17, the bone plate may include at least a first hole 424 and a second hole 428 having central axes 426, 428 respectively. First and second holes 424, 428 are configured in a substantially similar manner to holes 24, 28 of bone plate 10, such that they are capable of engaging a bone anchor, for example, the bone screw 100, the spiral blade 310 as previously described, or other types of bone anchors previously mentioned. It should be understood that first and second holes 424, 428 may be configured for engaging the head of a bone anchor by threaded engagement, interference or press fitting, or any other form of joining the plate with the anchor heads known to one of ordinary skill in the art. As shown, the first and second holes 424, 428 are preferably configured so as to form respective locking threaded engagement with bone screws 510, 515, similar to bone screw 100, having threaded heads 506 (not shown), shafts 504 and tips 505. The first and second holes 424, 428 may include an internal thread and have a conical taper from the upper surface 420 to the lower surface 422. The locked engagement fixes bone screws 510, 515 to the plate 410 such that shafts 504 extend along the central axes 426, 430 of the holes 424, 428 in the bone plate 410. Additionally, the first and second holes 424, 428 are preferably configured such that the central axes 426, 430 intersect at a point 432 below the lower surface 422 of the bone plate 410. The threaded engagement of bone screws 510, 515 with the threaded first and second holes 424, 428 may form a truss 528 beneath the bone surface, in a manner as previously described with respect to bone plate 10. The bone screw 510 may be substantially perpendicular to the lower surface 422 of the bone plate 410 or the exterior of the surface of the bone in which it is inserted. The bone screw 515 may be at an acute angle with respect to the lower surface of the bone plate or the exterior of the bone in which it is inserted. Screw 515 may contact bone screw 510 at the tip 105 of the bone screw 510, or anywhere along the shaft 104 of bone screw 510. According to one illustrative embodiment, the angle formed by the intersection of central axes 426, 430 may range from between about 30° to about 60°, although other angles are possible.

The first and second holes 424, 428 may be located in the same section of the bone plate 410, or alternatively the first hole 424 may be located in a section different from that of the second hole 428. Where the first and second hole 424, 428 are in the same section of the bone plate 410, the plane defined by the intersection of 426, 430 may be coplanar with a plane that bisects that same section of the bone plate 410 where the first and second holes 424, 428 are located. Alternatively, the plane defined by the intersection of central axes 426, 430 may be at an angle with respect to the plane that bisects bone plate 410 (not shown). The angle formed by the bisecting plane and the plane defined by intersecting central axes 426, 430 may range from about 0° to about 60°, or range to about 15°, or range from about 3° to about 6°.

Figure 21:
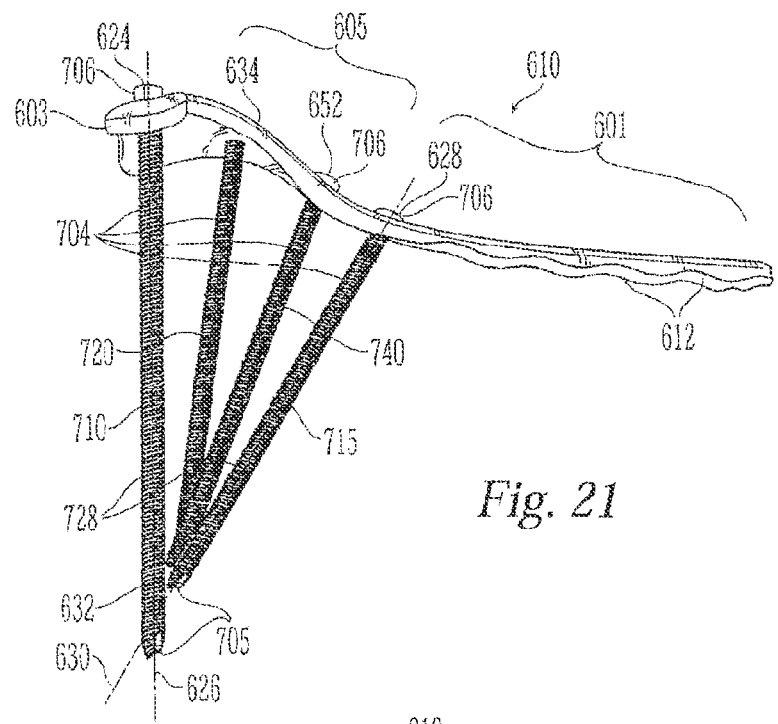
FIG. 21 is a perspective, partial view of the bone plate of FIG. 18.

A further embodiment, bone plate 610 shown in FIGS. 18-22, comprises first and second holes 624, 628, shown in FIG. 21, having first and second central axes 626, 630 intersecting at 632. A still further embodiment, bone plate 810, shown in FIGS. 25-29 comprises first and second holes 824, 828, shown in FIG. 25, having central axes 826, 830 intersecting 832. It is to be understood that first and second holes 624, 628 of bone plate 610 and first and second holes 824, 828 of bone plate 810 may be variably configurable as first and second holes 424, 428 of bone plate 410 described above. More specifically, the engagement of bone anchors with the plate 610 and/or 810 may fix the bone anchors at a predetermined angle to form, respectively, truss 728, shown in FIG. 21 and truss 1128, shown in FIG. 26, beneath the bone surface as presently described with respect to bone plates 10 and 410. The first and second bone screws may contact one another along their respective shafts or tips. In addition, bone plates 610 and 810 may selectively be anchored to bone such that their lower surfaces 622, 822 either contact the bone surface directly, with or without recesses 612, 812 for facilitating blood circulation over the fracture zone; or bone plates 610, 810 may be spaced from the bone surface at a relative distance.

FIGS. 15-27 show bone plates 410, 610, 810 and the respective connections of the first sections 401, 601, 801 and second sections 403, 603, 803 by the transition section 405, 605, 805 in various configurations; however, even other configurations are possible. Referring again to FIG. 16, the included angle $\lambda$, formed between the first and second central axes 402, 404 may be obtuse, ranging from about an angle of 195° to about 175°, or 120° to 160°, or preferably angle $\lambda$, measures about 153°. Alternatively the included angle may be substantially acute, ranging from an angle of about 15° to about 85°, preferably about 22°. Also, the angle $\lambda$, may be a right angle, in which the second section 403 is substantially perpendicular to the first section 401.

Figure 25:
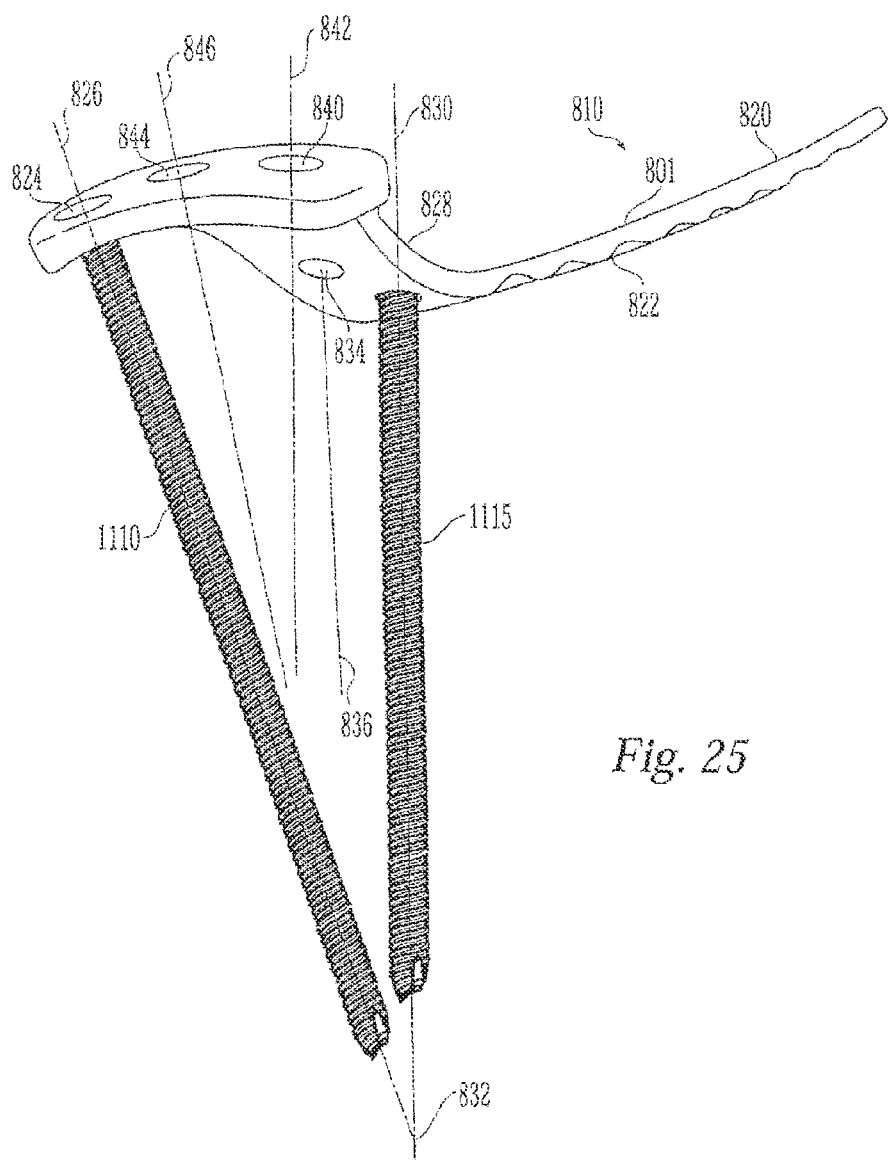
FIG. 25 is another perspective view of the bone plate of FIG. 23.

As shown in FIGS. 15-27, the first and second sections of bone plates 410, 610, 810 may have different lengths, e.g., the first section may be longer than the second section. The configurations are substantially similar to those shown and described in U.S. Patent Publication 2002/0183752 A1, the entire content of which is incorporated by reference thereto. Referring specifically to FIGS. 20 and 25, bone plates 610, 810 may, respectively, be substantially L-shaped or T-shaped. As shown in FIG. 19, the first section 601 may be located in a plane different from that of the second section 603. For instance, transition section 605 may be curved such that the lower surface 622 of the first section 601 is located in a first plane and the lower surface 622 of the second section 603 is located in a second plane different from the first plane. Alternatively or in addition thereto, the transition section 605 may be twisted so that the lower surface 622 of one side of the longitudinal axis 602, 604 is in a different from that of the lower surface 622 of the other side of the longitudinal axis 602, 604. This may be beneficial where the bone plates 410, 610, 810 have to be located over a curved portion of a bone, such as the medial and lateral condyles of the proximal tibia.

Figure 23:
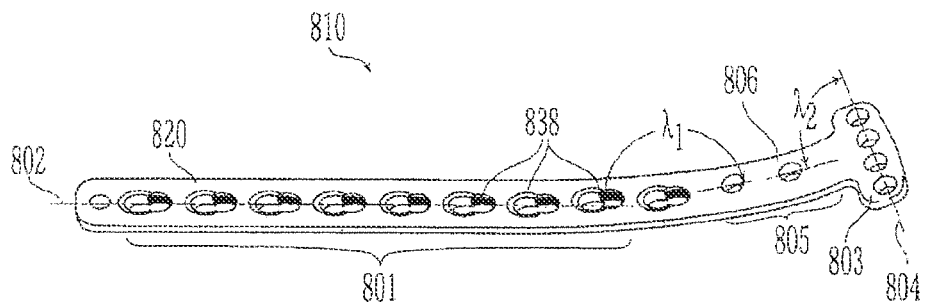
FIG. 23 is a top perspective view a further illustrative embodiment of a bone plate according to the present invention.
Figure 24:
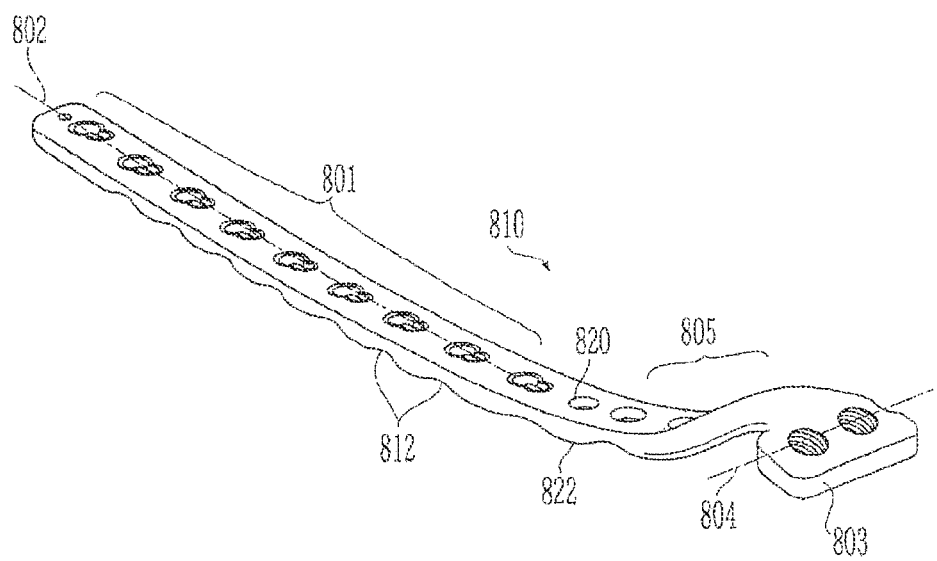
FIG. 24 is a perspective view of the bone plate of FIG. 23.

Referring now to FIG. 23, shown is another bone plate 810 in which the transition section 805 may define a third longitudinal axis 806 and may be configured so as to define a first included angle $\lambda_1$ with the first longitudinal axis 802 of the first section 801 and a second included angle $\lambda_2$ with the second longitudinal axis 804 of the second section 803. The transition section 805, may be bent, curved or twisted as previously described, or additionally, the transition section 805 may be twisted such that the upper surface 820 is substantially S-shaped. The first and second sections 401, 403; 601, 603; 801, 803 of bone plates 410, 610, 810 may also be twisted or bent to conform to the bone surface. For example, referring now to FIG. 20, shown is a cross-section view of the second section 603 of bone plate 610 in which the lower surface 622 may be bent or curved along the second longitudinal axis 604, so as to define a radius of curvature R. In addition, a portion of the first section 601 may be twisted about the first longitudinal axis 602.

The bone plates 410, 610, 810 may also be provided with at least a third hole defining a third central axis, in which the third hole may be variably configurable as the first and second holes 424, 428 previously described. The third hole may be engageable with the head or end portion of a bone anchor, for example bone screw 100 having a shaft 104 and tip 105. Specifically referring to FIGS. 18 and 19, an illustrative example, bone plate 610 includes third hole 634 having central axis 636. Third hole 634 may be configured for threaded locked engagement with a bone screw 100 so as to align the shaft 104 of bone screw 100 along the third central axis 636. The third central axis 636 of the third hole 634 may be disposed at such an angle so as to intersect with at least one of the first and second central axes 626, 630 of the first and second holes 624, 628. The third central axis 636 may be disposed at angle with respect to the plane formed by first and second central axes 626, 630.

Figure 22:
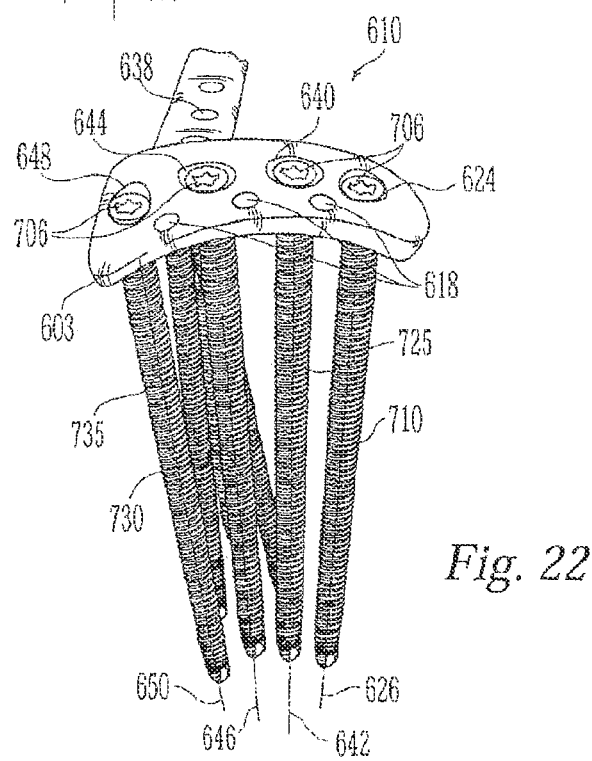
FIG. 22 is a frontal, partial, perspective view of the bone plate of FIG. 18.

Shown in the FIGS. 21 and 22 is bone plate 610 engaged with bone screws 710, 715, 720 respectively engaged with first, second and third holes 624, 628, 634. Bone screws 710, 715 are threadedly engaged with first and second holes 624, 628 to form truss 728 for rigidly anchoring the bone plate 610 to the fractured bone. The third bone screw 720, may be in threaded locked engagement with the bone plate 610 such that at least a portion of the shaft 104 of the third bone screw 720, preferably the tip 105, may touch or nearly touch at least one of the shafts of the first or second bone screws 710, 715 so as to further reinforce the truss 728 and the anchorage of bone plate 610. The third hole 634 may be located in the same section of the bone plate as either of the first and second holes 624, 628. Alternatively, the third hole 634 may be located in a section different from that or those of either of the first and second holes 624, 628. For example, as shown in FIG. 21, the third hole 634 is located in the transition section 605 with second hole 628. First hole 624 is located in the second section 603 of the bone plate 610.

As shown in FIGS. 15-27, bone plates 410, 610 and 810 may be provided with any number of holes as may be suitable for a specific surgical application. Any of these additional holes may be configured in a manner similar to and fully variable as first and second holes 424, 428 of bone plate 410, as previously described.

Referring now to FIGS. 21 and 22, the second section 603 of bone plate 610 may include additional holes 640, 644, 648 having central axes 642, 646, 650. As shown in FIG. 21, these additional holes may be configured for locked threaded engagement with heads 706 of bone screws 725, 730, 735 having shafts 704, in which the shafts 704 align with central axes 642, 646, 650. The central axes 642, 646, 650 may be disposed at such angles with respect to the first and second central axes 626, 630, that the shafts of bone screws 725, 730, 735 either touch, almost touch or are substantially parallel to bone screws 710, 715, which are shown engaged with first and second holes 624, 628. Additional holes similarly configured as 640, 644, 648 may be disposed in any of the first sections 401, 601, 801, second sections 403, 603, 803, or transition sections 405, 605, 805 of bone plates 410, 610, 810 as is necessary for the given surgical application. Shown in the illustrative embodiment of FIG. 21, transition section 605 includes hole 652 engaged with bone screw 740. Alternatively, the screw holes in the bone plate 610, can be configured such that a bone anchor, such as for example, conically threaded screw, can engage hole 624 and a second bone screw can engage hole 634 such that the screws contact or nearly contact to form a first truss structure. Alternatively or in addition thereto a third bone screw can engage hole 628 and a fourth bone screw can engage hole 648 such that the third and fourth screws contact or nearly contact to form a second truss structure. Alternatively, first bone screw and third bone screw may contact or nearly contact to form the first truss structure and second bone screw and fourth bone screw may contact or nearly contact to form the second truss structure. Alternatively or in addition, a fifth bone anchor may engage bone screw hole 652 and a sixth bone screw may engage hole 644. The fifth and sixth bone screws may contact or nearly contact to form yet a third truss structure.

First, second and third truss structures may be formed by any number of combinations of bone anchors in any number of configurations. Additionally, bone plate 610 may be provided with additional holes as is necessary to form the desired number of truss structures. Moreover, the first, second, third and any additional truss structures may or may not contact or nearly contact one or more of the other truss structures. Preferably, the second, third and additional truss structures may be angled so as to intersect a plane defined by the first truss structure.

Figure 26:
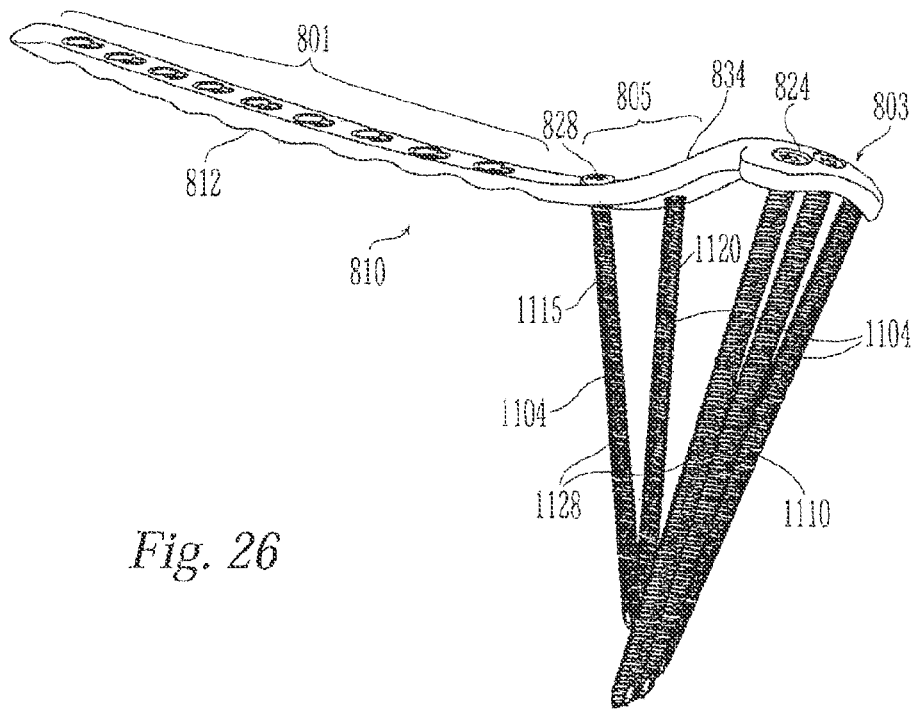
FIG. 26 is a further perspective view of the bone plate of FIG. 23.
Figure 27:
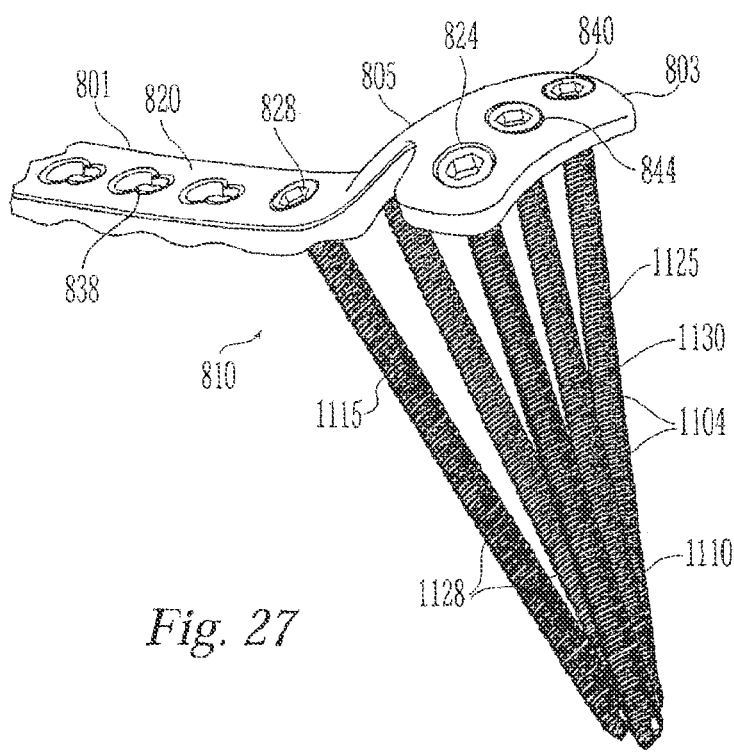
FIG. 27 is yet another perspective view of the bone plate of FIG. 23.

Another example is shown in the embodiment of bone plate 410. In FIG. 17, shown are holes 440, 444 disposed in the first section 401 spaced relative to the first and second holes 424, 428 located in the second section 403 of bone plate 410. Holes 440, 444 may be preferably configured for, respectively, threaded locked engagement with the threaded heads 506 (not shown) of bone anchors 525, 530 such that the shafts 104 may diverge from one another and diverge from the shafts 504 of bone fasteners 510, 515 engaged in first and second holes 424, 428. Another illustrative example is shown as the sixth embodiment, bone plate 810 in FIG. 25. First hole 824 is disposed in the second section 803, second hole 828 is disposed in the first section 801. Referring to FIGS. 25 and 26, the third hole 834 is located in the transition section 805 and is configured such that the shaft 1104 of bone screw 1120 engaged with third hole 834, would touch or nearly touch one of the shafts 1104 of bone screws 1110, 1115 engaged in first and second holes 824, 828. Additional holes 840, 844 are disposed in the second section 803 and are configured so as to engage bone screws 1125, 1130 in such a manner that the shafts 1104 would align in a direction toward the bone screws 1110, 1115 engaged in first and second holes 824, 828 so as to almost touch.

Bone plates 410, 610, 810 may yet further include additional holes, threaded or unthreaded, for receiving additional bone anchors for anchoring the bone plates 410, 610, 810 to bone. For example, bone plates 410, 610, 810 may include a plurality of combination holes 438, 638, 838, which are similar to the combination holes 38 described above in reference to FIGS. 11A and 11B. The combination holes 438, 638, 838 may all preferably be located in the first section 401, 601, 801 of the bone plates 410, 610, 810. Additionally, bone plates 410, 610, 810 may include one or more holes configured for receiving a guide wire or other instrument, for example, hole 72, as shown in FIG. 2 for receiving an instrument for applying compression to the fracture, or for example, as shown in FIG. 20, second section 603 includes a plurality of holes 618 configured for receiving a guide wire or other instrument.

The bone plates 10, 910, 410, 610, and 810 may vary in both length and width, but generally the length exceeds the width so as to define a generally longitudinal member. The length of the bone plates may range from about 50 mm. to about 500 mm. Bone plate 10 may preferably range in length from about 135 mm. to about 435 mm. Bone plate 910 may preferably range in length from about 145 mm. to about 480 mm. Bone plate 410 may preferably range in length from about 75 mm. to about 235 mm. Bone plate 610 may preferably range in length from about 81 mm. to about 240 mm.

Bone plate 810 may preferably range in length from about 105 mm to about 350 mm. Any section of bone plates 10, 910, 410, 610 and 810 may also vary in width from about 5 mm. to about 10 mm. to about 18 mm. Where one section of the bone plate is perpendicular to the other, the widest part of the bone plate may be as much as 35 mm. The thickness of the plates may vary as well from approximately 3 mm to about 5 mm. In addition the bone plates may vary in thickness in along its length. For example, shown in FIG. 1 portion 6 of bone plate 10 generally has a tapered portion. First sections 406, 606 and 806 may also generally have a tapered portion as well. All the bone plates discussed may have a tapered portion elsewhere throughout the bone plate or alternatively, the plate thickness may vary in cross-section.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

The invention claimed is:

1. A system comprising:
    a bone plate having a body that defines an upper surface which, in an operative configuration, faces away from a bone on which the plate is to be mounted and a lower surface, which in the operative configuration, faces the bone, the bone plate defining a first hole that extends through the body from the upper surface to the lower surface along a first hole axis, and a second hole that extends through the body from the upper surface to the lower surface; and
    a blade defining a proximal end, a distal end, and an axis that extends from the proximal end to the distal end, the blade further including a flute that extends at least between the proximal end and the distal end;
    wherein the proximal end of the blade is sized to be inserted into the second hole so as to attach to the bone plate when the blade is driven into bone such that the axis of the blade converges toward the first hole axis along a direction from the proximal end of the blade toward the distal end of the blade.

2. The system of claim 1, wherein the proximal end of the blade is sized to be inserted into the second hole so as to attach to the bone plate in the second hole such that the axis of the blade intersects the first hole axis.

3. The system of claim 2, wherein the axis of the blade defines an acute angle with respect to the first hole axis when the proximal end of the blade is attached to the bone plate in the second hole.

4. The system of claim 1, wherein the second hole extends through the body from the upper surface to the lower surface along a second hole axis that is angularly offset with respect to the first hole axis.

5. The system of claim 4, wherein the second hole axis intersects the first hole axis.

6. The system of claim 1, further comprising a bone anchor that is sized to be inserted into the first hole and into the bone along the first hole axis.

7. The system of claim 6, wherein the bone anchor includes a threaded head and a shaft that extends from the threaded head, and the first hole is threaded such that the threaded head is configured to threadedly attach to the bone plate in the first threaded hole.

8. The system of claim 7, wherein the bone anchor is a bone screw.

9. The system of claim 6, wherein the bone anchor includes a head and a shaft that extends from the head, and the head is sized to be press-fit or interference-fit to the bone plate in the first hole.

10. The system of claim 9, wherein the bone anchor is a bone screw.

11. The system of claim 6, wherein the bone anchor is sized to contact the blade when the bone anchor and the blade are attached to the bone plate in the first and second holes, respectively.

12. The system of claim 1, wherein the flute is a spiral flute.

13. The system of claim 1, wherein the blade includes a plurality of flutes that extend at least between the proximal end and the distal end.

14. The system of claim 13, wherein each of the flutes is a spiral flute.

15. The system of claim 1, wherein the blade defines an opening that extends therethrough.

16. The system of claim 15, wherein the opening extends along the longitudinal axis.

17. The system of claim 16, wherein the opening extends along the axis of the blade from the proximal end to the distal end.

18. The system of claim 1, wherein the axis of the blade extends toward the first hole axis along a direction from the proximal end to the distal end.

19. The system of claim 18, wherein the axis of the blade is linear.

20. The system of claim 1, wherein the body of the bone plate extends along a longitudinal axis and defines a first portion and a second portion that extends relative to the first portion along the longitudinal axis and has a curvature greater than that of the first portion in a direction of extension along the longitudinal axis, the first hole extends through the second portion, and the second hole extends through the first portion.

21. The system of claim 20, wherein the first portion that is substantially planar and the second portion is substantially curved for conforming to the head of a long bone.

22. The system of claim 20, wherein the curvature of the second portion is configured to conform to the head of a femur.

23. The system of claim 1, wherein the bone plate includes a third hole that extends through the body from the upper surface to the lower surface along a third hole axis.

24. The system of claim 23, further comprising bone anchors that each include a head and a shaft that extends from the head, the head of the each of the bone anchors configured to be inserted into the first and third holes, respectively, such that the shafts of the bone anchors extend along the first and third hole axes, respectively.

25. The system of claim 24, wherein engagement of the bone plate and the bone anchors define a truss formation.

26. The system of claim 23, wherein the body of the bone plate defines a first portion and a second portion, the second portion shaped to conform to a head of the bone, the second portion spaced from the first portion in a select direction, and each of the first and third holes is spaced from the second hole in the select direction.

27. The system of claim 26, wherein the axis of the blade converges toward each of the first hole axis and the third hole axis along the direction from the proximal end of the blade toward the distal end of the blade.

* * * * *